United States Patent
Pimentel et al.

(10) Patent No.: US 9,192,618 B2
(45) Date of Patent: *Nov. 24, 2015

(54) METHOD OF TREATING CONSTIPATION-PREDOMINANT IRRITABLE BOWEL SYNDROME

(71) Applicant: Cedars-Sinai Medical Center, Los Angeles, CA (US)

(72) Inventors: Mark Pimentel, Los Angeles, CA (US); Henry C. Lin, Albuquerque, NM (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/565,239

(22) Filed: Dec. 9, 2014

(65) Prior Publication Data

US 2015/0099713 A1 Apr. 9, 2015

Related U.S. Application Data

(60) Continuation of application No. 14/254,483, filed on Apr. 16, 2014, which is a continuation of application No. 12/030,758, filed on Feb. 13, 2008, which is a division of application No. 10/514,188, filed as application No. PCT/US03/16656 on May 20, 2003, now abandoned.

(60) Provisional application No. 60/382,172, filed on May 20, 2002.

(51) Int. Cl.
| | |
|---|---|
| A61K 9/00 | (2006.01) |
| A61K 31/01 | (2006.01) |
| A61K 31/74 | (2006.01) |
| A61K 31/351 | (2006.01) |
| A61K 31/405 | (2006.01) |
| A61K 31/7036 | (2006.01) |
| A61K 35/747 | (2015.01) |
| A61K 36/064 | (2006.01) |
| C12N 1/20 | (2006.01) |
| A61K 35/745 | (2015.01) |

(52) U.S. Cl.
CPC ........... *A61K 31/7036* (2013.01); *A61K 9/0053* (2013.01); *A61K 31/01* (2013.01); *A61K 31/351* (2013.01); *A61K 31/405* (2013.01); *A61K 31/74* (2013.01); *A61K 35/745* (2013.01); *A61K 35/747* (2013.01); *A61K 36/064* (2013.01); *C12N 1/20* (2013.01)

(58) Field of Classification Search
CPC ........... A61K 38/005; A61K 2300/00; A61K 31/7036; A61K 31/01; A61K 31/351; A61K 31/40; A61K 31/405; A61K 31/74; A61K 35/745; A61K 35/747; A61K 36/064; A61K 9/0053; A61K 31/137; A61K 31/155; A61K 31/22; A61K 31/366; A61K 45/06; A61K 31/554; A61K 31/785; A61K 31/00
See application file for complete search history.

(56) References Cited

U.S. PATENT DOCUMENTS

| | | | |
|---|---|---|---|
| 5,232,946 | A | 8/1993 | Hurnaus et al. |
| 5,447,850 | A | 9/1995 | McCann |
| 5,889,038 | A | 3/1999 | Lencer et al. |
| 5,977,175 | A | 11/1999 | Lin |
| 5,985,907 | A | 11/1999 | Wolin et al. |
| 6,036,950 | A | 3/2000 | Baker et al. |
| 6,299,774 | B1 | 10/2001 | Ainsworth et al. |
| 6,328,959 | B1 | 12/2001 | Kayar et al. |
| 6,368,591 | B1 | 4/2002 | Chen et al. |
| 6,495,567 | B1 | 12/2002 | Lencer et al. |
| 6,558,708 | B1 | 5/2003 | Lin |
| 6,562,629 | B1 | 5/2003 | Lin et al. |
| 6,805,852 | B2 | 10/2004 | Lin et al. |
| 6,861,053 | B1 | 3/2005 | Lin et al. |
| 2002/0028269 | A1 | 3/2002 | Verrips |
| 2002/0039599 | A1 | 4/2002 | Lin et al. |
| 2006/0246045 | A1 | 11/2006 | Pimentel et al. |
| 2008/0138320 | A1 | 6/2008 | Pimentel et al. |

(Continued)

FOREIGN PATENT DOCUMENTS

| | | |
|---|---|---|
| AU | 2003273141 | 8/2009 |
| CA | 2486585 | 7/2012 |
| EP | 1 609 852 A1 | 12/2005 |
| EP | 2 251 017 | 11/2010 |
| EP | 1 505 989 | 2/2011 |
| GB | 423083 A | 1/1935 |
| GB | 2 338 244 A | 12/1999 |
| JP | 60-133852 | 7/1985 |
| JP | 03-275630 | 12/1991 |
| JP | 08-310960 | 11/1996 |
| JP | 2005-526861 | 9/2005 |
| WO | WO 03/100023 | 12/2003 |

OTHER PUBLICATIONS

Dobson, C.L. et al., "The effect of oleic acid on the human ileal brake and its implications for small intestinal transit of tablet formulations," Pharm. Res. 16(1):92-96 (Jan. 1999).

(Continued)

*Primary Examiner* — Debbie K Ware
(74) *Attorney, Agent, or Firm* — Linda B. Huber; Nixon Peabody LLP

(57) ABSTRACT

Disclosed is a method of manipulating the rate of gastrointestinal transit in a mammalian subject. Also disclosed is the use, in the manufacture of a medicament for the treatment of constipation, of a selective inhibitor of methanogensis, a methanogen-displacing probiotic agent, or a prebiotic agent that inhibits the growth of methanogenic bacteria or promotes the growth of competing non-methanogenic intestinal flora. Alternatively, in accordance with the invention, is disclosed the use in the manufacture of a medicament for the treatment of diarrhea, of methane or a methane precursor, a methanogenic or other methane-enhancing probiotic agent, or a methanogenesis-enhancing prebiotic agent.

6 Claims, 11 Drawing Sheets

(56) References Cited

U.S. PATENT DOCUMENTS

2008/0182291 A1 7/2008 Pimentel et al.
2014/0228431 A1 8/2014 Pimentel et al.

OTHER PUBLICATIONS

Lin, H.C. et al., "Intestinal transit is more potently inhibited by fat in the distal (ileal brake) than in the proximal (jejunal brake) gut," Dig. Dis. Sci. 42(1):19-25 (Jan. 1997).
Lin, H.C. et al., "Jejunal brake: inhibition of intestinal transit by fat in the proximal small intestine," Dig. Dis. Sci., 41(2):326-29 (Feb. 1996).
Naidu, A.S., et al., "Probiotic spectra of lactic acid bacteria," Crit. Rev. Food Sci. Nutr. 38(1):13-126 (Jan. 1999).
Vanderhoof, J.A., et al., "Use of probiotics in childhood gastrointestinal disorders," J Pediatr Gastroenterol Nutr. 27(3):323-32 (Sep. 1998).
Tannock, G. W, "Probiotic properties of lactic acid bacteria: plenty of scope for R & D," Trends Biotechnol. 15(7):270-74 (Jul. 1997).
Salminen, S., et al., "Clinical uses of probiotics for stabilizing the gut mucosal barrier: successful strains and future challenges," Antoine Van Leeuwenhoek. 70(2-4):347-58 [1997] (Oct. 1996) (Review).
Chaucheyras F. et al., "In vitro $H_2$ utilization by ruminal acetogenic bacterium cultivated alone or in association with an archaea methanogen is stimulated by a probiotic strain of *Saccharomyces cerevisiae*," Appl Environ Microbiol 61(9):3466-7 (Sep. 1995).
Kontula, P., et al., "The effect of lactose derivatives on intestinal lactic acid bacteria," J. Dairy Sci. 82(2):249-56 (Feb. 1999).
Alander M., et al., "The effect of probiotic strains on the microbiota of the Simulator of the Human Intestinal Microbial Ecosystem (SHIME)," Int. J. Food Microbiol, 46(1):71-79 (Jan. 1999).
Spanhaak S., et al., "The effect of consumption of milk fermented by Lactobacillus casei strain Shirota on the intestinal microflora and immune parameters in humans," Eur. J. Clin. Nutr. 52(12):899-907 (Dec. 1998).
Charteris W.P., et al., "Antibiotic susceptibility of potentially probiotic *Lactobacillus* species," J. Food Prot. 61(12):1636-43 (Dec. 1998).
Wolf, B.W. et al., "Safety and tolerance of Lactobacillus reuteri supplementation to a population infected with the human immunodeficiency virus," Food Chem. Toxicol. 36(12):1085-94 (Dec. 1998).
Gardiner, G., et al., "Development of a probiotic cheddar cheese containing human-derivied Lactobacillus paracasei strains," Appl. Environ. Microbiol. 64(6):2192-99 (Jun. 1998).
Sameshima, T., et al., "Effect of intestinal Lactobacillus starter cultures on the behaviour of *Staphylococcus aureus* in fermented sausage," Int. J. Food Microbiol. 41(1):1-7 (May 1998).
Tuohy, K.M., et al., "The prebiotic effects of biscuits containing partially hydrolysed guar gum and fructo-oligosaccharides—a human volunteer study", Br J Nutr 86(3):341-8 (Sep. 2001).
McKay, L.F., et al., "Methane and hydrogen production by human intestinal anaerobic bacteria," Acta Pathol Microbiol Immunol Scand [B]. 90(3):257-60 (Jun. 1982).
Kerlin, P., et al., "Breath hydrogen testing in bacterial Overgrowth of the small intestine," Gastroenterology. 95(4):982-88 (Oct. 1988).
Strocchi, A., et al., "Detection of malabsorption of low doses of carbohydrate: accuracy of various breath H2 criteria," Gastroenterology 105(5):1404-10 (Nov. 1993).
De Boissieu, D., et al., "Small-Bowel bacterial overgrowth in children with chronic diarrhea, abdominal pain, or both," J Pediatr. 128(2):203-7 (Feb. 1996).
Lewindon, P.J., et al., "Bowel dysfunction in cystic fibrosis: importance of breath testing," J. Pediatr. Child Health 34(1):79-82 (Feb. 1998).
Corazza, G., et al., "Prevalence and consistency of low breath H2 excretion following lactulose ingestion. Possible implications for the clinical use of the H2 breath test," Dig. Dis. Sci, 38(11):2010-16 (Nov. 1993).

Riordan, S. M., et al., "The lactulose breath hydrogen test and small intestinal bacterial overgrowth," Am. J. Gastroentrol. 91(9):1795-1803 (Sep. 1996).
Swart, O.R., et al., "$^{13}C$ breath test in gastrointestinal practice," Scand. J. Gastroenterol. Suppl. 225:13-18 (1998).
Dellert, S.F., et al., "The $^{13}C$-xylose breath test for the diagnosis of small bowel bacterial overgrowth in children," J. Pediatr. Gastroenterol. Nutr. 25(2):153-58 (Aug. 1997).
King, C.E., et al., "Breath tests in the diagnosis of small intestinal bacterial overgrowth," Crit. Rev. Lab. Sci. 21(3):269-81 (1984).
Chang, C.S., et al., "Increased accuracy of the carbon-14 D-xylose breath test in detecting small-intestinal bacterial overgrowth by correction with the gastric emptying rate," Eur. J. Nucl. Med. 22(10):1118-22 (Oct. 1995).
King, C.E., et al., "Comparison of the 1-gram [14C]xylose, 10-gram lactulose-H2, and 80 gram glucose-H2 breath breath tests in patients with small intestine bacterial overgrowth," Gastroenterology 91(6):1447-51 (Dec. 1986).
Schneider, A., et al., "Value of the 14C-D-xylose breath test in patients with intestinal bacterial overgrowth," Digestion 32(2):86-91 (1985).
Drossman, D. A., et al., "Bowel patterns among subjects not seeing health care. Use of a questionaire to identify a population with bowel dysfunction," Gastroenterology. 83(3):529-34 (Sep. 1982).
Thompson, W.G., et al., "Functional bowel disorders in apparently healthy people." Gastroenterology. 79(2):283-8 (Aug. 1980).
Kumar, D., et al., "The irritable bowel syndrome: a paroxysmal motor disorder," Lancet. 2(8462):973-77 (Nov. 1985).
Grundy, D., "Mechanisms for the symptoms of irritable bowel disease—possible role of vagal afferents," In Neurogastroenterology from the Basics to the Clinics. H-J Drammer and MV Singer, Editors, Klumer Academic Publishers, Boston, 2000, pp. 659-663.
Silverman, D..S., et al., "Regional cerebral activity in normal and pathological perception of visceral pain," Gastroenterology. 112(1):64-72 (Jan. 1997).
Whitehead, W.E., et al., "Effects of stressful life events on bowel symptoms: Subjects with irritable bowel syndrome compared with subjects without bowel dysfunction," Gut 33(6):825-30 (Jun. 1992).
Thompson, W.G., et al., "Functional bowel disorders and functional abdominal pain. Rome II: A multinational consensus document on functional gastrointestinal disorders," Gut 45 Suppl. 2:II43-47 (Sep. 1999).
Kruis, W., et al., "A diagnostic score for the irritable bowel syndrome," Gastroenterology. 87(1):1-7 (Jul. 1984).
Sullivan, S.N., "A prospective study of unexplained visible abdominal bloating," N Z Med J. 107(988):428-30 (Oct. 1994).
Koide, A., et al., "Quantitative analysis of bowel gas using plain abdominal radiograph in patients with irritable bowel syndrome," Am J Gastroenterol, 92(7):1735-41 (Jul. 2000).
Pimentel, M., et al., "Eradication of small intestinal bacterial overgrowth reduces symptoms of irritable bowel syndrome," Am J Gastroenterol. 95(12):3503-6 (Dec. 2000).
Fiedorek, S.C., et al, "Breath methane production in children with constipation and encoparesis," J Pediatr Gastroenterol. 10(4):473-77 (May 1990).
Fass., R., et al., "Evidence and consensus-based practice guidelines ifor the diagnosis of irritable bowel syndrome." Arch Intern Med. 161(17):2081-88 (Sep. 2001).
Veldhuyzen Van Zanten, S.J., et al., "Design of treatment trials for functional gastrointestinal disorders," Gut. 45 Suppl II:II69-77 (Sep. 1999).
Whitehead, W.E., et al., "Definition of a responder in clinical trials for functional gastrointestinal disorders: reports on a symposium," Gut. 45 Suppl 2:II78-9 (Sep. 1999).
Camilleri, M., et al., "Efficacy and safety of alosetron in women with irritable bowel syndrome: a randomised, placebo-controlled trial," Lancet. 355(9209):1035-40 (Mar. 2000).
Bond, J.H. Jr., et al., "Investigation of small bowel transit time in man utilizing pulmonary hydrogen (H2) measurements," J Lab Clin Med. 85(4):546-555 (Apr. 1975).
Joseph, F. Jr., et al., "Breath testing: diseased versus normal patients," J Pediatr Gastroenterol. 7(5):787-8 (Sep.-Oct. 1988).

(56) References Cited

OTHER PUBLICATIONS

Galatola, G., et al., "Diagnosis of bacterial contamination of the small intestine using the 1g [14C] xylose breath test in various gastrointestinal diseases," Menerva Gastroenterologic Dietologica 37(3):169-75 (Jul.-Sep. 1991) (Abstract in English).

Nayak, A., et al., "Metronidazole relieves symptoms in irritable bowel syndrome: the confusion with so-called 'chronic amebiasis'," Indian J Gastroenterol 16(4):137-39 (Oct. 1997).

King, T.S., et al., "Abnormal colonic fermentation in irritable bowel syndrome," Lancet 352(9135):1187-89 (Oct. 1998).

Neal, K.R., et l., "Prevalence of gastrointestinal symptoms six months after bacterial gastroenteritis and risk facts for development of the irritable bowel syndrome: postal survey of patients," BMJ 314(7083):779-82 (Mar. 1997).

Collins, S.M., et al., "Stress, inflammation and the irritable bowel syndrome," Canadian Journal of Gastroenterology. 13 Suppl:47A-49A (Mar. 1999).

Weaver, G.A., et al., "Incidence of methanogenic bacteria in a sigmoidoscopy population: an association of methanogenic bacteria and diverticulosis," Gut. 27(6):698-704 (Jun. 1986).

Bjorneklett, A., et al., "Bacterial overgrowth in jejunal and ileal disease," Scand J Gastroenterol. 18(2):289-98 (Mar. 1983).

McKay, L.F., et al., "Methane excretion in man—a study of breath, flatus and feces," Gut 26(1):69-74 (Jan. 1983).

Castiglione, F., et al. "Orocecal transit time and bacterial overgrowth in patients with Crohn's disease," J Clin Gastroenterol. 31(1):63-66 (Jul. 2000).

Bentley, D.W., et al., "The microflora of the human ileum and intrabdominal colon: results of direct needle aspiration at surgery and evaluation of the technique," J Lab Clin Med. 79(3):421-9 (Mar. 1972).

Gorbach, S.L., "Intestinal Microflora," Gastroenterology. 60(6):1110-29 (Jun. 1971).

Nichols, R.L., et al., "Ileal microflora in surgical patients," J Urol. 105(3):351-3 (Mar. 1971).

Plaut, A.G., et al, "Studies of intestinal microflora. 3. The microbial flora of human small intestinal mucosa and fluids," Gastroenterology 53(6):868-73 (Dec. 1967).

Soares et al. "Breath methane associated with spin colonic transit time in children with chronic constipation," J. Clin. Gastroenterol. Jul. 2005; vol. 39, No. 6, pp. 512-515.

Chatterjee et al. "The degree of breath methane production in IBS correlates with the severity of constipation," Am. J. Gastroenterology 2007; 102: 837-841.

Novick et al. "A randomized, double-blind, placebo-controlled trial of tegaserod in female patients suffering from irritable bowel syndrome with constipation," Aliment. Pharmacol. Ther. 2002; 16: 1877-1888.

Pimentel et al. "Methane, a gas produced by enteric bacteria, slows intestinal transit and augments small intestinal contractile activity," Am. J. Physiol. Gastrointest. Liver Physiol. 2006; 290: G1089-G1095.

Pimentel et al. "Neomycin improves constipation-predominant irritable bowel syndrome in a fashion that is dependent on the presence of methane gas: Subanalysis of a donble-blind randomized controlled study," Dig. Dis. Science 2006; 51: 1297-1301.

Olesen et al. "Efficacy, safety, and tolerability of fructooligosaccharides in the treatment of irritable bowel syndrome," Am. J. Clin. Nutr. 2000; 72: 1570-1575.

Niedzielin et al. "A controlled, double-blind, randomized study on the efficacy of Lactobacillus plantarum 299V in patients with irritable bowel syndrome," Euro. J. of Gastroenterology & Hepatology: Oct. 2001, vol. 13, Issue 10, pp. 1143-1147.

Nobaek, et al. "Alteration of intestinal microflora is associated with reduction in abdominal bloating and pain in patients with irritable bowel syndrome," Am. J. Gastroenterology (2000) 95, 1231-1238.

Thompson, W. Grant. "Probiotics for irritable bowel syndrome: a light in the darkness?" Euro. J. of Gastroenterology & Hepatology: Oct. 2001, vol. 13, Issue 10, pp. 1135-1136.

Cann, P.A., et al., "Irritable bowel syndrom: relationship of disorders in the transit of a single solid meal to symptom patterns," Gut 24(5):405-11 (May 1983).

Read, N.W., et al., "Simultaneous measurement of gastric emptying, small bowel residence and colonic filling of a solid meal by the use of the gamma camera," Gut. 27(3):300-8 (Mar. 1986).

Hutchinson, R., et al., "Scintigraphic measurement of ieocaecal transit in irritable bowel syndrome and chronic idiopathic constipation," Gut 36(4):585-9 (Apr. 1995).

Rhodes, J.M., et al., "The lactulose hydrogen breath test as a diagnostic test for small bowel bacterial overgrowth," Scand J Gastroenterol. 14(3):333-6 (1979).

Rutgeerts, P., et al., "Ileal dysfunction and bacterial overgrowth in patients with Crohn's disease," European J Clin Invest. 11(3):199-206 (Jun. 1981).

Funayama, Y., et al., "Monitoring and antibacterial treatment for postoperative bacterial overgrowth in Crohn's disease," Dis Colon Rectum. 42(8):1072-7 (Aug. 1999).

Peled, Y., et al., "Factors affecting methane production in humans. Gastrointestinal diseases and alterations of colonic flora," Dig Dis Scr. 32(3):267-71 (Mar. 1987).

Melcher, E.A., et al., "Methane production and bowel function parameters in healthy subjects on low-and high fiber diets," Nutrition and Cancer. 16(2):85-92 (1991).

Levitt, M D., et al., "Hydrogen and methane production in man," Ann NY Acad Sci. 150(1):75-81 (Feb. 1968).

Engels et al., Symptomless Colonisation by Clostridium Difficile and Risk of Diarrhoea, The Lancet, (Jun. 6, 1998), p. 1733, 351:9117, London, Great Britain.

Nguyen et al., Diarrhea Caused by Enterotoxigenic Bacteroides Fragilis in Children Less Than 5 Years of Age in Hanoi, Vietnam, Anaerobe, (Feb. 2005), pp. 109-114, 11:1-2, London, Great Britain.

Kehrer et al. Modulation of Irinotecan-Induced Diarrhea by Cotreatment With Neomycin in Cancer Patients. Clinical Cancer Research, May 2001, 7(1), pp. 1136-1141.

Black et al., An Overview of The Clinical Safety Profile of Atorvastatin (Lipitor), A New HMG-CoA Reductase Inhibitor, Archives of Internal Medicine, (Mar. 23, 1998), 158(6):577-584.

Bakker-Arkema et al., Safety Profile of Atotvastatin-Treated Patients With Low LDL-Cholesterol Levels, Atherosclerosis, (2000). 149(1): 123-129.

The Merck Index (11th Edition), (1989). Entry 5225, p. 844.

Hoeg et al., Effects of Combination Cholestyramine-Neomycin Treatment on Plasma Lipoprotein Concentrations in Type II Hyperlipoproteirtemia, American Journal of Cardiology, 55(11):1282-1286, 1985.

Hoshimo et al., Maldigestion/Malabsorption in the Various Gastrointestinal and Liver Diseases. Results of Breath Hydrogen and Methane Analysis, Digestion & Absorption, (1998), 21(1):55-60.

Soares et al. "Metano no ar Expirado de Criancas com Constipacao Cronica Funcional," Arq. Gastroenterol., vol. 39, No. 1, Jan./Mar. 2002; pp. 66-72.

METHOD OF TREATING CONSTIPATION-PREDOMINANT IRRITABLE BOWEL SYNDROME

CROSS-REFERENCE TO RELATED APPLICATIONS

This application claims the benefit of priority under 35 U.S.C. §120 as a continuation of U.S. patent application Ser. No. 14/254,483, filed Apr. 16, 2014, which is a continuation of U.S. patent application Ser. No. 12/030,758, filed Feb. 13, 2008, which is a divisional application of U.S. patent application Ser. No. 10/514,188, filed Sep. 19, 2005, which is a National Phase of International Application No. PCT/US03/16656, filed May 20, 2003, which designated the U.S. and that International Application was published under PCT Article 21(2) in English; this application also claims the benefit of priority to 35 U.S.C. §119(e) of U.S. Provisional Application No. 60/382,172, filed May 20, 2002, herein incorporated by reference in their entirety.

BACKGROUND OF THE INVENTION

Discussion of the Related Art

Irritable bowel syndrome (IBS) is a common gastrointestinal disorder seen in more than 15% of the population (1,2).

Over the last few years, progress has been made in characterizing irritable bowel syndrome (IBS). Studies have demonstrated altered gut motility (3), peripheral (4) and central (5) sensory dysfunction, as well as an exaggerated response to stress (6) in this syndrome. However, there is no finding that can be identified in a majority of patients and by extension, there is no diagnostic test that is associated with IBS. As a result, investigators have created complex diagnostic schema such as the Rome criteria to help diagnose and categorize the syndrome (7,8).

One consistent clinical finding in IBS is gas in combination with bloating and visible distention (9,10). Koide et al. recently found small intestinal gas to be significantly increased in IBS compared to controls (11) regardless of whether subjects conform to diarrhea, constipation or pain subgroups.

Excessive small intestinal gas can occur as a result of increased production of gas within the gut by bacterial fermentation. Hydrogen and methane are common gases excreted during breath testing (43). Although hydrogen production appears more ubiquitous, methane production is seen in 36-50% of healthy subjects (27, 41, 42). In particular, methane is noted to be common in diverticulosis (25), and less prevalent in diarrheal conditions such as Crohn's or ulcerative colitis (26-28). Recent data suggests that children with encopresis have excessive breath methane on lactulose breath test ("LBT"; 13). This finding has not been extended to adults with constipation-predominant IBS.

A condition known to produce excessive small bowel gas is small intestinal bacterial overgrowth (SIBO). Small intestinal bacterial overgrowth is a condition in which the small bowel is colonized by excessive amounts of upper or lower gastrointestinal tract flora. Although there are many conditions associated with SIBO, recent studies have demonstrated an increased prevalence of SIBO in irritable bowel syndrome (IBS) (12) and it is a recognized cause of diarrhea in inflammatory bowel disease (IBD) (28, 39, 40).

There is some support for the association between altered breath testing results and enteric flora in IBS. In one study, 56% of diarrhea predominant IBS subjects were found to have a positive $^{13}$C-xylose breath test (20). In another study, flagyl was reported to be superior to placebo in reducing clinical symptoms in IBS (21). The authors in that paper were uncertain of the mechanism for this improvement.

One method of diagnosing SIBO is the lactulose breath test (LBT) where overgrowth is considered to be present if a greater than 20 ppm rise in breath hydrogen or methane concentration is observed within 90 minutes of oral administration of lactulose (19).

In a recent study, we suggested that a large percent (78%) of IBS subjects has SIBO as diagnosed by lactulose breath test (12). Some workers criticize the reliability of LBT to diagnose SIBO since in the identification of any infectious process, culture is the gold standard. The main issue with culture is accessibility. Riordan, et al. compared breath testing to direct culture and found the breath test to lack reliability (29). This and other similar studies were confounded by their selection of subjects who had surgically altered anatomy predisposing to the development of upper GI tract SIBO. Since SIBO (in surgically naïve patients) is often an expansion of colonic bacteria, the direction of expansion is retrograde involving first the distal small intestine. As such, direct culture is only practical in the patient whose SIBO is so severe that the bacteria has expanded proximally into the duodenum or proximal jejunum.

Regardless of some skepticism about the reliability of LBT to diagnose SIBO, there are similarities between SIBO and IBS. Bloating, a feature of SIBO, is also classically associated with IBS (10). In SIBO, bloating is due to small intestinal fermentation of nutrients. Until recently, gas studies in IBS have been limited to the investigation of flatus. Yet, even these studies suggest the presence of excessive bacteria in IBS. King, et al found the production of hydrogen by IBS subjects to be five-fold elevated implying excessive enteric bacteria (22). Recently, data suggest that IBS patients have excessive gas and that this gas is localized to the small intestine (11). However, the contrasting diarrhea and constipation predominant subgroups in IBS remain unexplained.

The speed of transit through the small intestine is normally regulated by inhibitory mechanisms located in the proximal and distal small intestine known as the jejunal brake and the ileal brake. Inhibitory feedback is activated to slow transit when end products of digestion make contact with nutrient sensors of the small intestine. (E.g., Lin, H. C., U.S. Pat. No. 5,977,175; Dobson, C. L. et al., *The effect of oleic acid on the human ileal brake and its implications for small intestinal transit of tablet formulations*, Pharm. Res. 16(1):92-96 [1999]; Lin, H. C. et al., *Intestinal transit is more potently inhibited by fat in the distal (Ileal brake) than in the proximal (jejunal brake) gut*, Dig. Dis. Sci. 42(1):19-25 [1997]; Lin, H. C. et al., *Jejunal brake: inhibition of intestinal transit by fat in the proximal small intestine*, Dig. Dis. Sci., 41(2):326-29 [1996a]).

Methane in the intestinal lumen has never before been reported to affect the rate of gastrointestinal transit.

SUMMARY OF THE INVENTION

The present invention relates to a method of manipulating the rate of gastrointestinal transit in a mammalian subject, including a human patient. The method involves: (a) increasing the rate of gastrointestinal transit by causing the partial pressure of methane in the subject's intestines to be decreased; and (b) decreasing the rate of gastrointestinal transit by causing the partial pressure of methane in the subject's intestines, for example in the distal gut, to be increased.

Thus, by practicing the inventive method to increase the rate of gastrointestinal transit, constipation and disorders exhibiting constipation can be treated in subjects in whom abnormally elevated intestinal methane levels are detectable (e.g., in cases of constipation-predominant irritable bowel syndrome [IBS], pseudoobstruction, colonic inertia, postoperative ileus, encopresis, hepatic encephalopathy, or medication-induced constipation). In accordance with this embodiment of the present invention, the partial pressure of methane in the subject's intestines can be decreased by administering to the subject's intestinal lumen a selective inhibitor of methanogenesis, such as monensin, or a methanogen-displacing probiotic agent, or a prebiotic agent that inhibits the growth of methanogenic bacteria or promotes the growth of competing non-methanogenic intestinal flora.

Consequently, the present invention is also directed to the use in the manufacture of a medicament for the treatment of constipation, of a selective inhibitor of methanogenesis, or of a methanogen-displacing probiotic agent, or of a prebiotic agent that inhibits the growth of methanogenic bacteria or promotes the growth of competing non-methanogenic intestinal flora.

And alternatively, by practicing the inventive method to decrease the rate of gastrointestinal transit, patients with diarrhea and disorders exhibiting diarrhea can be treated (e.g., cases of diarrhea-predominant IBS, Crohn's disease, ulcerative colitis, celiac disease, microscopic colitis, dumping syndrome, rapid transit, short bowel syndrome, post-gastrectomy syndrome, diabetic diarrhea, hyperemesis, or antibiotic-associated diarrhea). In accordance with this embodiment of the present invention, the partial pressure of methane in the subject's intestines can be increased by administering methane gas to the intestinal lumen of the subject, for example into the distal segment of the intestine of the subject, or by administering to the subject a methanogenic probiotic agent or methogenesis-enhancing prebiotic agent.

Consequently, the present invention is also directed to the use in the manufacture of a medicament for the treatment of diarrhea, of methane or a methane precursor, or of a methanogenic or other methane-enhancing probiotic agent, or of a methogenesis-enhancing prebiotic agent.

These and other advantages and features of the present invention will be described more fully in a detailed description of the preferred embodiments which follows.

DETAILED DESCRIPTION OF THE PREFERRED EMBODIMENTS

Figure 1:
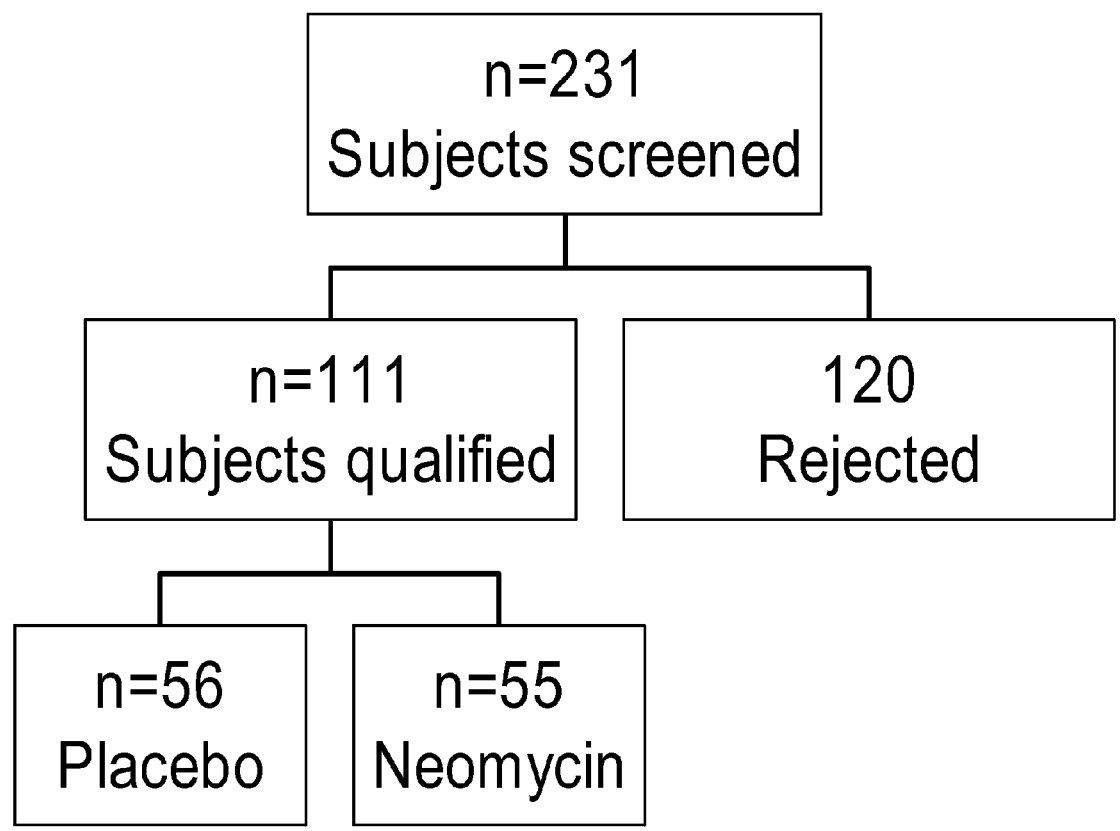
FIG. 1 shows a patient flow chart for a double-blind, randomized, placebo-controlled study confirming that an abnormal lactulose breath test is more prevalent in IBS than normal controls, and that antibiotic treatment in IBS leads to an improvement in symptoms and that this is based on antibiotic-induced normalization of breath test.

In accordance with the present invention, the partial pressure of methane in the subject's intestines can be decreased by administering to the subject's intestinal lumen a selective inhibitor of methanogenesis, such as monensin. Useful selective inhibitors of methanogenesis include HMG-CoA reductase inhibitors known in the art (e.g., U.S. Pat. No. 5,985,907) that selectively inhibit the growth of methanogenic bacteria without significantly inhibiting the growth of non-methanogens, for example in the distal gut or colon of the subject.

Alternatively, or concurrently, in accordance with the present invention, the partial pressure of methane in the subject's intestines can be decreased by administering to the subject's intestinal lumen a methanogen-displacing probiotic agent to inhibit the growth of methanogenic bacteria therein, for example, an inoculum of a lactic acid bacterium, *bifidobacterium*, or probiotic *Saccharomyces* species, e.g., *S. cerevisiae*. (A. S. Naidu et al., *Probiotic spectra of lactic acid bacteria*, Crit. Rev. Food Sci. Nutr. 39(1):13-126 [1999]; J. A. Vanderhoof et al. [1998]; G. W. Tannock, *Probiotic properties of lactic acid bacteria: plenty of scope for R & D*, Trends Biotechnol. 15(7):270-74 [1997]; S. Salminen et al., *Clinical uses of probiotics for stabilizing the gut mucosal barrier: successful strains and future challenges*, Antonie Van Leeuwenhoek 70(2-4):347-58 [1997]; Chaucheyras F. et al., *In vitro $H_2$ utilization by a ruminal acetogenic bacterium cultivated alone or in association with an archaea methanogen is stimulated by a probiotic strain of Saccharomyces cerevisiae*, Appl Environ Microbiol 61(9):3466-7 [1995]). The inoculum is typically administered in a pharmaceutically acceptable ingestible formulation, such as in a capsule, or for some subjects, consuming a food supplemented with the inoculum is effective, for example a milk, yoghurt, cheese, meat or other fermentable food preparation. Useful probiotic agents include *Bifidobacterium* sp. or *Lactobacillus* species or strains, e.g., *L. acidophilus*, *L. rhamnosus*, *L. plantarum*, *L. reuteri*, *L. paracasei* subsp. *paracasei*, or *L. casei* Shirota, (P. Kontula et al., *The effect of lactose derivatives on intestinal lactic acid bacteria*, J. Dairy Sci. 82(2):249-56 [1999]; M. Alander et al., *The effect of probiotic strains on the microbiota of the Simulator of the Human Intestinal Microbial Ecosystem (SHIME)*, Int. J. Food Microbiol. 46(1):71-79 [1999]; S. Spanhaak et al., *The effect of consumption of milk fermented by Lactobacillus casei strain Shirota on the intestinal microflora and immune parameters in humans*, Eur. J. Clin. Nutr. 52(12):899-907 [1998]; W. P. Charteris et al., *Antibiotic susceptibility of potentially probiotic Lactobacillus species*, J. Food Prot. 61(12):1636-43 [1998]; B. W. Wolf et al., *Safety and tolerance of Lactobacillus reuteri supplementation to a population infected with the human immunodeficiency virus*, Food Chem. Toxicol. 36(12):1085-94 [1998]; G. Gardiner et al., *Development of a probiotic cheddar cheese containing human-derived Lactobacillus paracasei strains*, Appl. Environ. Microbiol. 64(6):2192-99 [1998]; T. Sameshima et al., *Effect of intestinal Lactobacillus starter cultures on the behaviour of Staphylococcus aureus in fermented sausage*, Int. J. Food Microbiol. 41(1):1-7 [1998]).

Alternatively, or concurrently, in accordance with the present invention, the partial pressure of methane in the subject's intestines can be decreased by administering to the subject's intestinal lumen a prebiotic agent that inhibits the growth of methanogenic bacteria or promotes the growth of competing non-methanogenic intestinal flora. (E.g., Tuohy K M et al., *The prebiotic effects of biscuits containing partially hydrolysed guar gum and fructo-oligosaccharides—a human volunteer study*, Br J Nutr 86(3):341-8 [2001]).

In accordance with the present invention, the partial pressure of methane in the subject's intestines can be increased by administering methane to the subject's intestinal lumen. Accordingly, methane can be administered directly to the intestine by infusion through a tube, preferably via the rectum, but other access routes for intubation to the intestine are also useful. Alternatively, methane can be administered to the intestinal lumen by providing a medicament comprising a catalyst and chemical substrate (i.e., a "methane precursor") to the intestinal lumen, where they come in contact to produce methane in situ. For example, the catalyst and substrate can be administered in separate control release tablets, which release their contents in the desired location in the intestine.

Alternatively, in accordance with the present invention, the partial pressure of methane in the subject's intestines can be increased by administering to the subject's intestinal lumen a methane-enhancing probiotic agent. A "methane-enhancing" probiotic agent is one that effectively enhances the partial pressure of methane in the subject's intestinal lumen. The methane enhancing probiotic agent can be a methanogenic bacterium, such as *Methanobrevibacter smithii*, or certain *Bacteroides* spp. or *Clostridium* spp. (see, e.g., McKay L F et al., *Methane and hydrogen production by human intestinal anaerobic bacteria*, Acta Pathol Microbiol Immunol Scand [B] 90(3):257-60 [1982]), or an organism that can enhance the growth of intestinal methanogens, such as *Clostridium butyricum*.

Alternatively, or concurrently, in accordance with the present invention, the partial pressure of methane in the subject's intestines can be increased by administering to the subject's intestinal lumen a prebiotic agent that enhances the growth of methanogenic bacteria.

As the term is commonly used in the art, the "proximal" segment of the small bowel, or "proximal gut", comprises approximately the first half of the small intestine from the pylorus to the mid-gut. The distal segment, or "distal gut" includes approximately the second half, from the mid-gut to the ileal-cecal valve.

Representative methods of administering include giving, providing, feeding or force-feeding, dispensing, inserting, injecting, infusing, perfusing, prescribing, furnishing, treating with, taking, ingesting, swallowing, eating or applying. Administration of inhibitors, probiotic agents, or prebiotic agents, is by well known means, including most preferably oral administration and/or enteral administration.

Detection of intestinal methane and other gases, while not essential to the practice of the invention, can be accomplished, if desired, by any suitable means or method known in the art. For example, one preferred method is breath testing. (E.g., P. Kerlin and L. Wong, *Breath hydrogen testing in bacterial overgrowth of the small intestine*, Gastroenterol. 95(4):982-88 [1988]; A. Strocchi et al., *Detection of malabsorption of low doses of carbohydrate: accuracy of various breath $H_2$ criteria*, Gastroenterol. 105(5):1404-1410 [1993]; D. de Boissieu et al., [1996]; P. J. Lewindon et al., *Bowel dysfunction in cystic fibrosis: importance of breath testing*, J. Paedatr. Child Health 34(1):79-82 [1998]). Breath hydrogen or breath methane tests are based on the fact that many obligately or facultatively fermentative bacteria found in the gastrointestinal tract produce detectable quantities of hydrogen or methane gas as fermentation products from a substrate consumed by the host, under certain circumstances. Substrates include sugars such as lactulose, xylose, lactose, sucrose, or glucose. The hydrogen or methane produced in the small intestine then enters the blood stream of the host and are gradually exhaled.

Typically, after an overnight fast, the patient swallows a controlled quantity of a sugar, such as lactulose, xylose, lactose, or glucose, and breath samples are taken at frequent time intervals, typically every 10 to 15 minutes for a two- to four-hour period. Samples are analyzed by gas chromatography or by other suitable techniques, singly or in combination. A variable fraction of the population fails to exhale appreciable hydrogen gas during intestinal fermentation of lactulose; the intestinal microflora of these individuals instead produce more methane. (G. Corazza et al., *Prevalence and consistency of low breath $H_2$ excretion following lactulose ingestion. Possible implications for the clinical use of the $H_2$ breath test*, Dig. Dis. Sci. 38(11):2010-16 [1993]; S. M. Riordan et al., *The lactulose breath hydrogen test and small intestinal bacterial overgrowth*, Am. J. Gastroentrol. 91(9); 1795-1803 [1996]). A non-digestible substrate other than lactulose can optionally be used.

Another useful method of detecting intestinal gases, such as methane, is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human host, such as lactulose, xylose, mannitol, or urea. (E.g., G. R. Swart and J. W. van den Berg, $^{13}C$ *breath test in gastrointestinal practice*, Scand. J. Gastroenterol. [Suppl.] 225:13-18 [1998]; S. F. Dellert et al., *The 13C-xylose breath test for the diagnosis of small bowel bacterial overgrowth in children*, J. Pediatr. Gastroenterol. Nutr. 25(2):153-58 [1997]; C. E. King and P. P. Toskes, *Breath tests in the diag-* nosis of small intestinal bacterial overgrowth, Crit. Rev. Lab. Sci. 21(3):269-81 [1984]). A poorly digestible substrate is one for which there is a relative or absolute lack of capacity in a human for absorption thereof or for enzymatic degradation or catabolism thereof.

Suitable isotopic labels include $^{13}C$ or $^{14}C$. For measuring methane or carbon dioxide, suitable isotopic labels can also include $^2H$ and $^3H$ or $^{17}O$ and $^{18}O$, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}C$, $^3H$, or $^{15}O$, breath samples can be analyzed by gas chromatography with suitable radiation detection means. (E.g., C. S. Chang et al., *Increased accuracy of the carbon-14 D-xylose breath test in detecting small-intestinal bacterial overgrowth by correction with the gastric emptying rate*, Eur. J. Nucl. Med. 22(10):1118-22 [1995]; C. E. King and P. P. Toskes, *Comparison of the 1-gram [$^{14}C$]xylose, 10-gram lactulose-$H_2$, and 80-gram glucose-$H_2$ breath tests in patients with small intestine bacterial overgrowth*, Gastroenterol. 91(6):1447-51 [1986]; A. Schneider et al., *Value of the $^{14}C$-D-xylose breath test in patients with intestinal bacterial overgrowth*, Digestion 32(2):86-91 [1985]).

The preceding are merely illustrative and non-exhaustive examples of methods for detecting small intestinal bacterial overgrowth.

The invention will now be described in greater detail by reference to the following non-limiting examples.

EXAMPLES

Example 1

Methane Excretion on Breath Test has a Positive Predictive Value of 100% for Constipation-Predominant IBS

In a double-blind, randomized, placebo-controlled study, we confirm that an abnormal lactulose breath test is more prevalent in IBS than normal controls, and that antibiotic treatment in IBS leads to an improvement in symptoms and that this is based on antibiotic-induced normalization of breath test. Secondly, lactulose breath test profiles are evaluated to show that gaseous constituents vary among IBS subgroups. In this study, we show that methane excretion on breath test has a positive predictive value of 100% for constipation predominant IBS. This is another important step in linking SIBO and IBS.

A. Materials and Methods
Study Population

Study subjects were recruited by advertising in local newspapers, radio and IBS support groups throughout the greater Los Angeles area. To avoid referral bias, subjects were not recruited through the GI motility clinic or any gastroenterology practice based at Cedars-Sinai Medical Center. Subjects were included if they met Rome I criteria for IBS (7). Rome I was chosen as it does not prejudice between diarrhea and constipation, and no peer-review publications were available to validate Rome II as a diagnostic strategy (14). Subjects were excluded if they had antibiotics within the previous three months, a previous lactulose breath test (LBT), or a history of diabetes, thyroid disease, intestinal surgery (except cholecystectomy or appendectomy), connective tissue disease, narcotic use or known gastrointestinal disease. Subjects with renal insufficiency, hearing impairment, probiotic use or allergy to aminoglycosides were also excluded. Approval from the institutional review board and written informed consent from the participating subjects were obtained.

In an initial comparison, 15 sex-matched normal controls were identified based on the absence of all Rome 1 criteria. These subjects underwent lactulose breath testing and the prevalence of abnormal breath test was compared to subjects with IBS.

Study Design

Subjects presented to the GI Motility Laboratory having fasted from 7:00 p.m. the night before. They were instructed not to ingest legumes or a heavy meal for dinner the night prior to evaluation. Good oral hygiene was recommended and smoking was not permitted on the day of testing.

Prior to the LBT, subjects completed a symptom questionnaire asking them to grade nine IBS symptoms (abdominal pain, diarrhea, constipation, bloating, sense of incomplete evacuation, straining, urgency, mucus and gas) on a severity score of 0-5 as has been previously used and recommended (15-17). All questions were answered based on their recall of the preceding 7 days (17).

Subjects then underwent a LBT by ingesting 10 g of lactulose (Inalco Spa, Milano, Italy, packaged by Xactdose Inc., South Beloit, Ill.) followed by 1-2 ounces of water after an initial baseline breath sample. Breath samples were then collected at 15 minute intervals for 180 minutes. End expiratory breath samples were taken to ensure alveolar gas sampling. Samples were analyzed for hydrogen, methane and carbon dioxide using a Model SC, Quintron gas chromatograph (Quintron Instrument Company, Milwaukee, Wis.). Carbon dioxide measurements were used to correct for the quality of alveolar sampling. Measurements were plotted graphically as previously described (12). Patients and investigators were blinded to the result of the breath test.

All subjects were randomized by personnel not associated with the study to receive, in a double blind fashion, either neomycin (500 mg) (Teva pharmaceuticals, USA, Sellersville, Pa.) or matching placebo twice daily for 10 days. Seven days after completion of the antibiotic or placebo, subjects returned for a repeat questionnaire and LBT. A seven day follow up was chosen since in our experience the abnormal breath test in IBS can recur as early as two weeks after antibiotic normalization. As part of the follow up questionnaire, subjects were asked to subjectively rate the amount of improvement they experienced as a percent normalization of bowel function and repeated their perceived severity of the 9 bowel symptoms described earlier. Compliance was assessed by pill count. To comply with institutional review board requirements, follow-up LBT results could not be blinded so patients could seek appropriate medical therapy for their test result.

At the completion of enrollment, all initial and follow-up breath tests were coded and randomized by personnel not involved in the interpretation of the test. A blinded reviewer (M.P.) interpreted the results and was asked to categorize the breath tests based on whether the test met the criteria for normal LBT. A normal LBT was defined as, no rise of breath hydrogen ($H_2$) or methane ($CH_4$) concentration before 90 minutes of lactulose, with a definitive rise never more than 20 ppm during 180 minutes of measurement (18, 19, 37, 38). Studies that fell out of this range were categorized as abnormal. A second set of criteria for breath test interpretation was also used whereby the traditional 2 peaks to suggest bacterial overgrowth were required. Since the two peak method was not well not as well validated a technique (37) as the parts per million (ppm), this finding was only used to compare the prevalence of this finding to healthy controls.

Measures of Outcome

Data were analyzed using an intention-to-treat method. The primary outcome measure was based on a composite score (CS) calculated from the 3 main IBS symptoms (abdominal pain, diarrhea and constipation each on a scale from 0-5) to generate a score out of 15 (most severe). This was done to account for the severity of all potential IBS subgroups. Since other IBS symptoms (such as straining) would worsen or improve depending on whether patients started with diarrhea or constipation, respectively, minor criteria were not included in the CS. In addition, as reduction in colonic organisms could result in an improvement in gas and bloating, irrespective of bacterial overgrowth, gaseous symptoms too were excluded from the score. The percent improvement in the CS was then compared between placebo and neomycin. In addition, the overall percent bowel normalization as determined by patient reporting was likewise compared.

The prevalence of a true clinical response was then determined and compared between placebo and neomycin. A true clinical response was defined as a ≥50% reduction in CS. Secondarily, a true clinical response was also assessed based on subjects reporting their overall percent bowel normalization. A ≥50% normalization implied a true clinical response. This method of analysis closely followed the multinational consensus recommended guidelines for data analysis in IBS clinical studies (16).

Secondary endpoints included a similar analysis of gender subgroups. Subsequently, IBS subgroups were identified whereby diarrhea predominant IBS was deemed present when diarrhea severity (0-5 scale) was greater than constipation in any individual subject. The opposite proportion determined constipation predominance. This means of identifying diarrhea and constipation predominant subgroups was chosen since criteria for these subgroups are not validated and based subjectively on physician interview (14). This approach further reduced bias since subjects would not be aware of the interest in subgrouping their predominant feature.

A post hoc analysis was then conducted on all abnormal breath test results to determine if the type of gas produced on LBT was related to IBS subgroup. The abnormal breath tests were divided into two abnormal test groups: hydrogen production only and any methane production. The relationship between constipation predominant IBS and diarrhea predominant IBS to the type of gas seen was determined. Subsequently, in a more objective fashion, the severity score for diarrhea and constipation were then compared between gas types. Finally, a score based on the difference between constipation and diarrhea severity (i.e., constipation score minus diarrhea score; "C-D") was determined. The C-D was used to examine the relative weight of constipation to diarrhea in individual subjects (the more positive the score the greater the dominance the constipation was compared to diarrhea). Subjects with identical score for constipation and diarrhea severity were excluded from these analyses. This C-D score was also compared between gas types.

Finally, to support the principal that the abnormal test in IBS was not due to rapid transit, the mean breath test profile in constipation and diarrhea predominant IBS was compared. Since it is suggested in the literature that diarrhea predominant IBS is associated with rapid transit (34-36) and constipation predominant IBS with slow transit (34, 35), the hydrogen profile should be different in both groups.

Statistical Analysis

The number of subjects enrolled in the study was determined based on the detection of a 10% difference between placebo and neomycin. This further assumed a 15% variance and an $\alpha=0.05$ with power of 90% in a 2-sided analysis.

Quantitative data were compared using the Student's t-test with results expressed as mean±S.E. Comparisons of qualitative data utilized Fisher's Exact Test for comparison of IBS subjects to healthy controls. All other comparisons of qualitative data utilized Chi-square. A 1-way ANOVA was used to compare the results of the 3 groups: placebo treated, neomycin with unsuccessful normalization of LBT and neomycin treated with successful normalization of LBT.

B. Results

Subject Demographics

Two-hundred and thirty-one subjects were screened (FIG. 1). Of these, 111 met enrollment criteria. However, 10 of these 111 subjects had incomplete data (6 in neomycin group and 4 in placebo group). The specific reasons for incomplete data were, voluntary premature withdrawal (n=3), no follow up breath test (n=4), failure to show up for follow up (n=1), no follow-up questionnaire (n=1) and premature withdrawal by subject due to severe diarrhea (n=1). Despite the incomplete data, these subjects were included in the intention-to-treat analyses and they were counted as no (0%) improvement. The baseline characteristics were similar for the neomycin and placebo groups (Table 1, below).

TABLE 1

Comparison of demographics between placebo and neomycin.

| Characteristic | Placebo | Neomycin | p-value |
|---|---|---|---|
| n | 56 | 55 | |
| Age | 41.9 ± 0.2 | 44.7 ± 0.2 | NS |
| Sex (F/M) | 27/29 | 34/21 | NS |
| Baseline Composite Score | 8.7 ± 0.4 | 8.8 ± 0.3 | NS |
| Abnormal breath test [n (%)] | 47 (84) | 46 (84) | NS |
| Diarrhea predominant IBS [n (%)] | 21 (40)> | 25 (48)* | NS |
| Constipation predominant IBS [n (%)] | 20 (38)> | 18 (35)* | NS |
| Other IBS subgroup [n (%)] | 11 (21)> | 7 (13)* | NS |

Data are mean ± S.E.
Baseline composite score = pain severity + diarrhea score + constipation score (each on a scale from 0-5) before treatment.
Other IBS subgroup = subjects with constipation severity = diarrhea severity.
*Only 52 subjects in the neomycin group completed the questionnaire sufficiently to determine this result.
>Only 52 subjects in the placebo group completed the questionnaire sufficiently to determine this result.
NS = not significant.

Case-Control Comparison

IBS subjects had a higher prevalence of abnormal LBT than sex-matched controls with 93 out of 111 (84%) subjects fulfilling these criteria compared to 3 out of 15 (20%) sex-matched controls (OR=26.2, CI=4.7-103.9, p<0.00001). When comparing the prevalence of abnormal LBT with double peak, 55 out of 111 IBS subjects (50%) were positive compared to 2 out of 15 healthy controls (13%) (p=0.01).

Primary Outcome Measures

In the intention-to-treat analysis, neomycin resulted in a 35.0±0.7% reduction in CS compared to a 11.4±1.3% reduction in the placebo group (p<0.05). In the subgroup of patients with abnormal baseline LBT (n=93), neomycin produced a 35.4±0.8% reduction in CS versus a 3.7±1.6% reduction in the placebo group (p<0.01). No difference was seen in subjects with a normal baseline breath test although a higher placebo rate was reported in this very small group (51%).

Ninety-one out of the 111 subjects completed their percent bowel normalization question after treatment. Of these 91 subjects, neomycin resulted in a 40.1±5.3% reported bowel normalization compared to 15.1±3.6% for placebo (p<0.001). Amongst the subgroup of subjects with abnormal initial breath tests, neomycin resulted in a 44.8±5.6% normalization compared to 11.0±3.3% for placebo (p<0.00001).

Neomycin was more likely to result in a true clinical response than placebo. Among all subjects receiving neomycin, 24 out of 55 (43%) experienced a ≥50% improvement in CS versus 13 out of 56 (23%) in the placebo group (OR=4.3, CI=1.05-6.3, p<0.05). In the subgroup of subjects with abnormal breath tests, 21 out of 46 (46%) receiving neomycin had a clinical response compared to 7 out of 47 (15%) in the placebo group (OR=4.8, CI=1.62-14.7, p<0.01). Using patient's subjective report of percent bowel normalization, in the whole group of subjects who answered this question (n=91), 50% of subjects receiving neomycin had a true clinical response in contrast to 17% of subjects getting placebo (OR=4.8, C1=1.7-14.4, p<0.01). In those with abnormal initial breath test, 55% of neomycin and 11% of placebo treated subjects had a true clinical response (OR=9.6, CI=2.5-39.7, p<0.0001). Finally, 7 out of the 8 subjects (88%) who had a normal follow up LBT after neomycin reported more than 50% normalization of bowel function.

Of the 111 subjects, only the 101 subjects with complete data were used in the remainder of the analyses.

Figure 2:
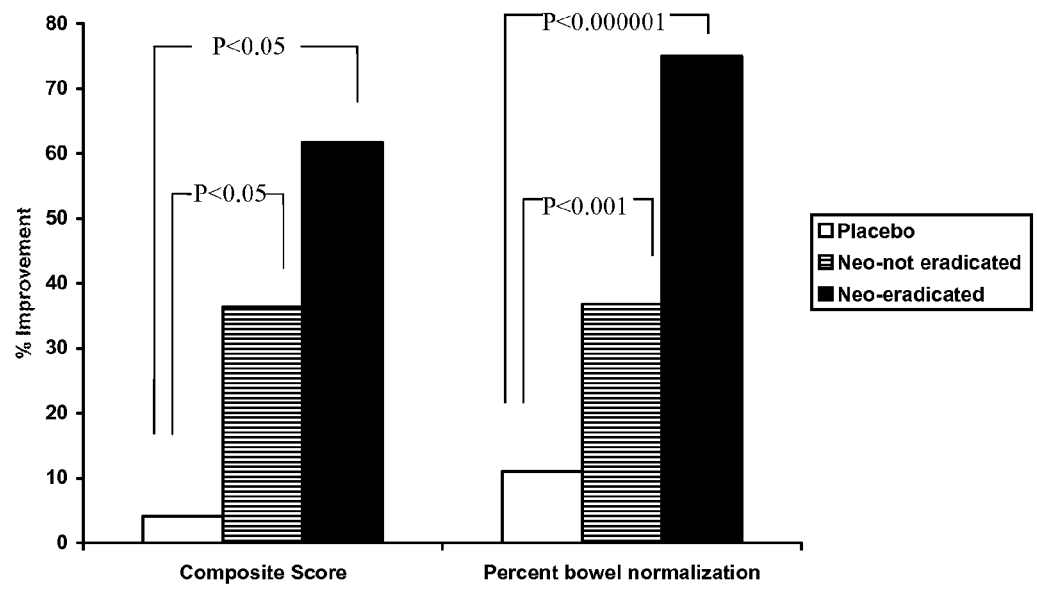
FIG. 2 shows percent improvement in composite score based on treatment and success in normalizing the LHBT. Data=mean % reduction in composite score; the difference in the composite score was significant (p=0.01, 1-way ANOVA). The difference in patient reported improvement was also significant (p<0.000001, 1-way ANOVA). In the neomycin treated groups, the data were analyzed according to success of treatment. Neo=Neomycin.

Of 84 out of 101 subjects with an abnormal baseline LBT, 41 were treated with neomycin. Eight out of 41 (20%) achieved normalization of LBT. One out of 43 subjects in the placebo group went from an abnormal breath test to normal. A significant difference in symptom response was seen depending on the outcome of treatment in these abnormal subjects. Specifically, the percent reduction in CS was different in the following 3 groups: subjects receiving placebo (4.1±11.7%), neomycin-treated group that did not achieve LBT normalization (34.4±6.2%) and neomycin-treated group with LBT normalization (61.7±9.4%) (p=0.01, 1-way ANOVA) (FIG. 2). Using patients self-report of percent bowel normalization, the 3 groups were more different. Subjects receiving placebo reported 11.0±3.7% normalization, subjects receiving neomycin but not successful normalization of LBT, 36.7±6.1% and those subjects with normal follow up LBT after neomycin reporting 75.0±6.4% bowel normalization (p<0.0000001, 1-way ANOVA).

Neomycin, although statistically more effective than placebo, was only able to normalize the breath test 20% of the time. This may be due to the large numbers and types of enteric organisms (30-33) or bacterial resistance.

Transit Comparison

When the mean hydrogen breath test profile was compared between diarrhea and constipation predominant IBS subjects, there was no evidence that diarrhea predominance had earlier hydrogen appearance (data not shown). In fact, diarrhea and constipation profiles were both virtually superimposable and not different at any time point with a mean of >20 ppm at 90 minutes in both groups.

Adverse Events

One subject developed profuse watery diarrhea while taking placebo. The cause of the diarrhea was later found to be food poisoning. Two of the enrolled subjects were found to have other diagnoses. The first subject had an 8 cm mass in the abdomen. The surgical specimen demonstrated non-Hodgkin's lymphoma. This subject was in the placebo group. The second subject was noted to have urinary retention, which precipitated bowel complaints. The second subject was in the neomycin group. Both these subjects had a normal initial LBT. Both were included as part of the intention-to-treat analysis.

Effect of Gender

Figure 3:
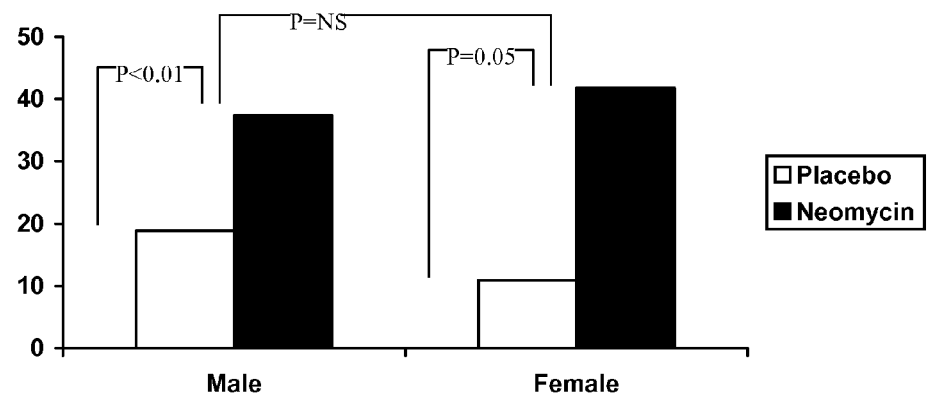
FIG. 3 shows a comparison of percent reported bowel normalization between and within gender groups; NS=not significant.

Both male and female subjects were noted to have a significantly greater improvement in percent bowel normalization over placebo (FIG. 3). Furthermore, there was no difference in response rate between male and female patients.

Type of Gas and IBS Subgroup

Figure 4:
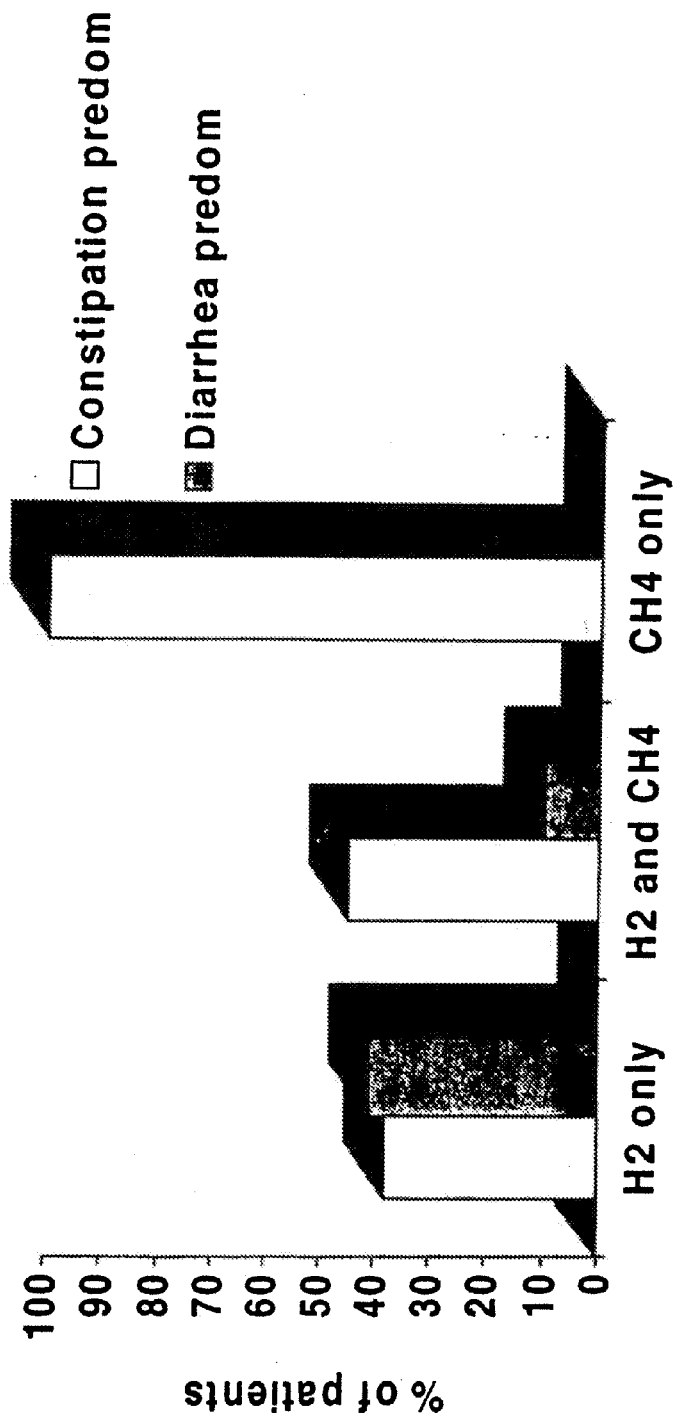
FIG. 4 show the pattern of gas production with IBS symptom type, i.e., constipation-predominant IBS (unshaded bars; p<0.00001) versus diarrhea-predominant IBS (shaded bars; p<0.001).
Figure 5:
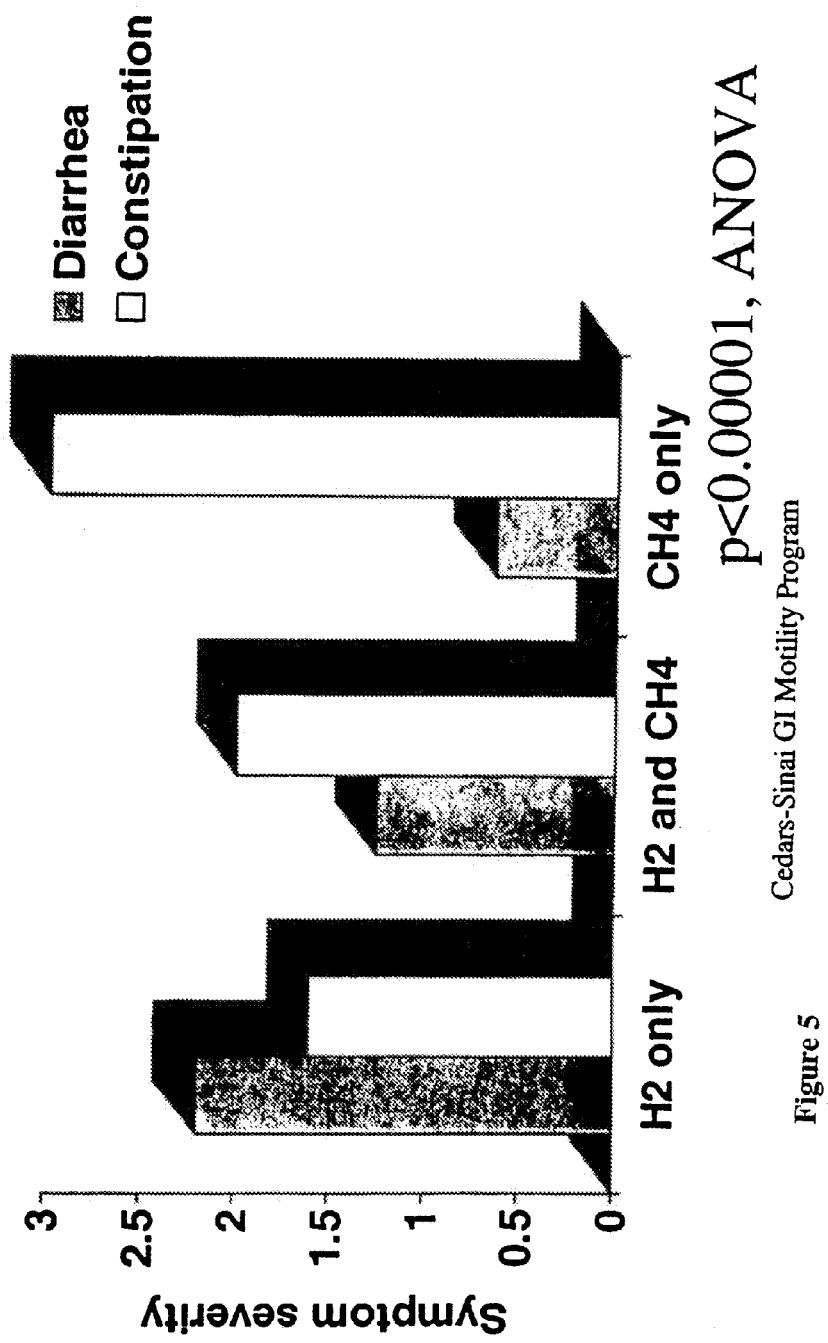
FIG. 5 show the pattern of gas production in IBS patients (n=65) with respect to symptom severity in those with constipation-predominant IBS (unshaded bars; p<0.00001) versus those with diarrhea-predominant IBS (shaded bars; p<0.00001).

The type of gas produced by IBS subjects on LBT was predictive of their subtype of IBS amongst the 84 subjects with abnormal baseline. After exclusion of subjects with no gas production (n=4) and subjects where constipation severity was equal to diarrhea (n=15), 34 diarrhea predominant and 31 constipation predominant IBS subjects were analyzed. Twelve out of 31 constipation-predominant subjects (39%) excreted methane whereas no methane excretion was seen in the 34 diarrhea predominant subjects (OR=∞, CI=3.7-4.3, p<0.001, positive predictive value=100%) (Table 2, below; and FIG. 4). The severity of constipation was 4.1±0.3 in subjects with methane excretion but only 2.3±0.2 in non-methane excretors (p<0.01) (Table 3, below). In a similar comparison, the C-D was 2.8±0.5 in methane excretors and −0.7±0.3 for hydrogen excretors (p<0.00001) (Table 3; and see FIG. 5).

TABLE 2

Comparison of IBS subgroups based on methane and hydrogen excretion with abnormal breath test.

|  | Hydrogen | Methane |
| --- | --- | --- |
|  | (n = 65)* | |
| Diarrhea | 34 | 0 |
| Constipation | 19 | 12 |

*After exclusion of subjects with no gas production (n = 4), normal breath test (n = 17) and subjects where the diarrhea severity = constipation severity (i.e. neither predominant) (n = 15).
P < 0.001 between groups.

TABLE 3

Evaluation of the severity of constipation or diarrhea based on methane production on baseline breath test.

|  | No methane | Methane | p-value |
| --- | --- | --- | --- |
| Constipation severity | 2.3 ± 0.2 | 4.1 ± 0.3 | <0.001 |
| Diarrhea severity | 3.0 ± 0.2 | 1.4 ± 0.4 | <0.001 |
| C-D score* | −0.7 ± 0.3 | 2.8 ± 0.5 | <0.00001 |

*C-D score represents the difference between severity of constipation and diarrhea.
This was done to show an increased relative weight of constipation to diarrhea with methane excretors.

Regardless of any argument as to whether the breath test reliably detects SIBO or not, the data in this study support a role of the LBT in IBS treatment as it is only when the subsequent LBT is normal that the greatest symptom improvements are realized.

Although the discussion has thus far focused on the abnormal breath test representing abnormal intestinal flora, another possible interpretation need to be discussed. The abnormal breath tests seen in the study could represent rapid transit. Studies have suggested that small bowel transit is accelerated in diarrhea predominant IBS (34-36). Similar studies suggest that subjects with constipation predominant IBS have delayed transit (34, 35). If transit is the explanation for the abnormal breath test findings then subjects with constipation predominant IBS should have delayed gas rise on breath test. On the contrary, in our study, breath tests were abnormal irrespective of subgroup of IBS suggesting that transit alone cannot explain the findings. Furthermore, the clinical improvement in a composite score (consisting of diarrhea, constipation and abdominal pain) that depends on the normalization of the LBT cannot be explained on the basis of transit alone.

In summary, in this double-blind, randomized, placebo-controlled study, we found a higher prevalence of abnormal lactulose breath tests in IBS patients than controls, indicative of SIBO. In addition, we found that antibiotics were more effective than placebo in terms of symptom improvement and normalization of the breath test produced an even greater improvement of IBS symptoms, substantiating results from a previous study (12). Furthermore, we found that methane excretion on breath testing was highly associated with the constipation predominant subgroup of IBS. The ability to identify subgroups of IBS based on LBT further supports the association between SIBO and IBS. The presence of SIBO in IBS patients is consistent with the existence of persistent antigenic challenge in IBS.

Example 2

Administration of Methane to the Distal Gut Slows Gastrointestinal Transit

We now show that methane administered directly to the distal gut produces a slowing of gastrointestinal transit. In dogs equipped with duodenal (10 cm from pylorus) and mid-gut (160 cm from pylorus) fistulas, intestinal transit was compared across an isolated 150 cm test segment (between fistulas) while the proximal segment of the gut was perfused with pH 7.0 phosphate buffer at 2 mL/min for 90 minutes. Room air (n=three dogs) or methane (n=three dogs) was delivered into the distal gut as a 180-ml bolus at time 0. Sixty minutes after the start of the perfusion, 20 µCi of $^{99m}$Tc-DTPA (diethylenetriaminepentaacetic acid) was delivered as a bolus into the proximal segment of the gut. Intestinal transit was then measured by counting the radioactivity of 1 ml samples collected every 5 minutes from the diverted output of the mid-gut fistula.

Intestinal transit was calculated by determining the area under the curve (AUC) of the cumulative percent recovery of the radioactive marker in the control (air administration) and experimental (methane administration) dogs. The square root values of the AUC (Sqrt AUC), where 0=no recovery by 30 minutes and 47.4=theoretical, instantaneous complete recovery by time 0, were compared for the control and experimental animals, using 2-way repeated measures ANOVA.

Figure 6:
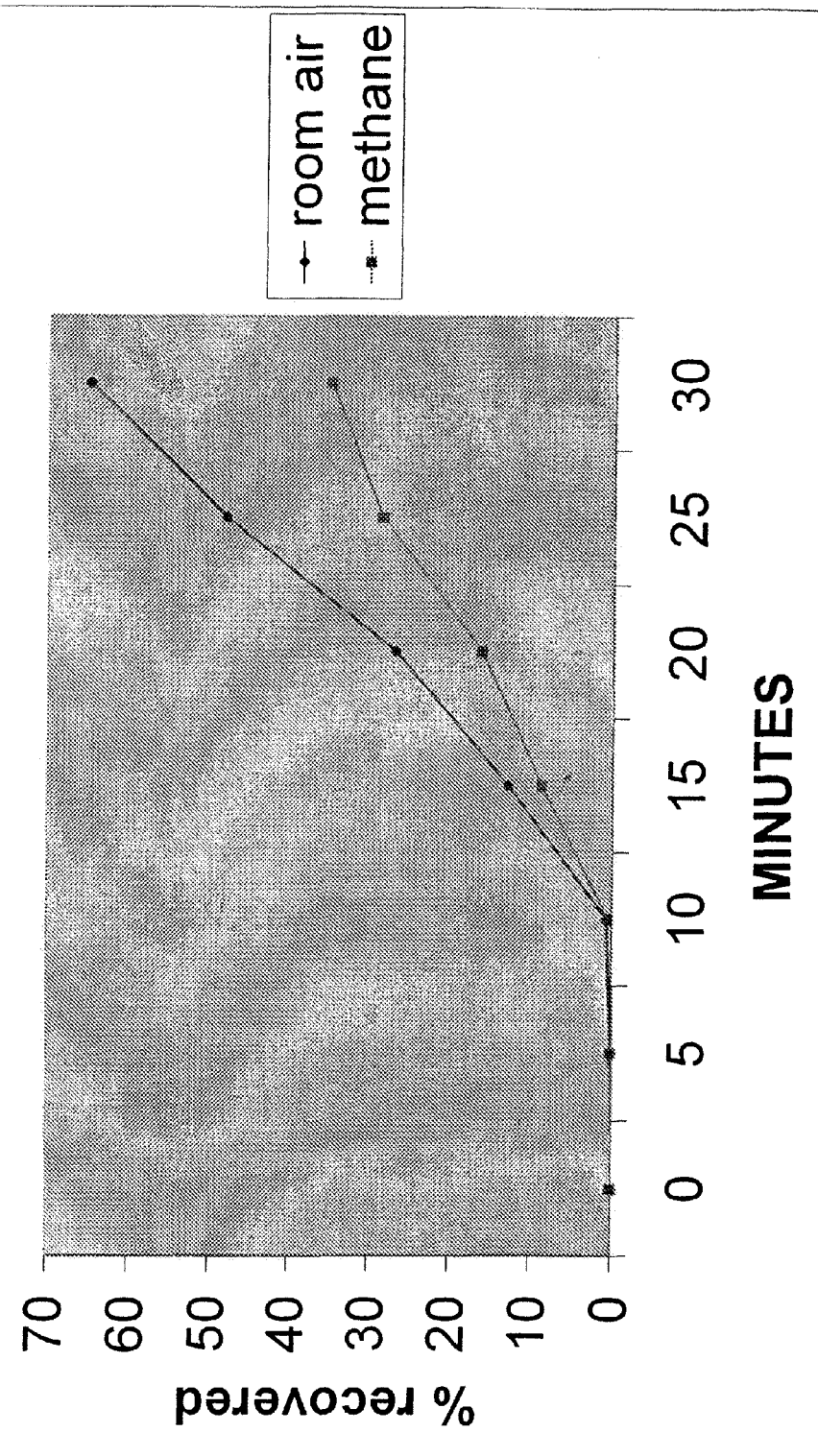
FIG. 6 illustrates the effect on intestinal transit in dogs administered 180 ml of room air (circles) or methane gas (squares) by bolus delivery to the distal gut. Methane slowed intestinal transit.

The results shown in FIG. 6, demonstrate that administration of methane to the distal gut substantially slowed the rate of intestinal transit in the experimental group, compared to the control.

Example 3

The following study confirmed and further investigated the relationship between gastrointestinal complaints (specifically, diarrhea and constipation) in TBS-diagnosed subjects with SIBO and gas excretion on LBT in a large prospectively collected database. The prevalence of gas excretion patterns in IBS and the predominantly diarrheal conditions of Crohn's disease and ulcerative colitis were also compared.

A. Materials and Methods.

Patient Population

Consecutive patients referred for a lactulose breath test (LBT) to the Cedars-Sinai Medical Center, GI Motility Program from 1998-2000 completed a questionnaire designed to assess bowel symptoms as previously described (12) after approval from the institutional review board. Subjects were requested to rate the severity of nine symptoms (diarrhea, constipation, abdominal pain, bloating, sense of incomplete evacuation, straining, urgency, mucus, and gas) on a scale of 0-5, 0 signifying the absence of the symptom. The questionnaire also inquired whether subjects had Crohn's disease (CD) or ulcerative colitis (UC). Of subjects reporting a history of inflammatory bowel disease (IBD), only those whose diagnosis had been confirmed by the Cedars-Sinai Inflammatory Bowel Disease Center were included in the analysis. The diagnosis of IBS was identified if subjects fulfilled Rome I criteria (7). Subjects found to have both IBD and IBS were assigned to the IBD subgroup.

Subjects with conditions predisposing to rapid transit (short bowel syndrome, gastrectomy, etc.), those taking narcotic medications, and those without evidence of overgrowth on LBT were excluded.

Lactulose Breath Test (LBT)

After an overnight fast, subjects completed the questionnaire. A baseline breath sample was then obtained after which subjects ingested 10 g of lactulose syrup (Inalco Spa, Milano, Italy, packaged by Xactdosc Inc., South Beloit, Ill.). This was followed by 1 ounce of sterile water. Breath samples were then collected every 15 minutes for 180 minutes. Each sample was analyzed for hydrogen, methane, and carbon dioxide gas concentration within 15 minutes of collection using a Model SC Quintron gas chromatograph (Quintron Instrument Company, Milwaukee, Wis.). $CO_2$ was analyzed to correct for the quality of the alveolar sampling.

Three different abnormal gas patterns were described upon completion of the test:

1. Hydrogen positive breath test: Rise in breath hydrogen concentration of >20 ppm within 90 minutes of lactulose ingestion (18, 19, 37, 38).

2. Hydrogen and methane positive breath test: Rise in both breath hydrogen and methane concentrations of >20 ppm within 90 minutes of lactulose ingestion.

3. Methane positive breath test: Rise in breath methane concentration of >20 ppm within 90 minutes of lactulose ingestion.

Data Analysis

For all subjects with SIBO, mean diarrhea and constipation severity scores among the three abnormal gas patterns were compared.

Based on symptom severity scores, the entire IBS group was further subdivided into diarrhea-predominant and constipation-predominant subgroups. Constipation-predominant IBS was identified if a subject's severity score exceeded his or her diarrhea severity score, whereas the reverse applied for diarrhea-predominant IBS. Subjects who had a constipation severity score equal to the diarrhea severity score (indeterminate pattern) were excluded from the IBS subgroup analysis. The percentage of IBS subjects within each abnormal gas pattern who reported constipation-predominant or diarrhea-predominant symptoms was tabulated. The prevalence of methane production between the IBS subgroups was also compared.

Subsequently, a mean C-D score was obtained by calculating the difference between the constipation and diarrhea severity scores. This was used to examine the relative weight of constipation to diarrhea in individual subjects. The C-D score was compared among the three abnormal breath gas patterns in the group as a whole and among IBS subjects.

Finally, the prevalence of each of the three abnormal gas patterns was evaluated in subjects with CD and UC. The prevalence of methane production was contrasted between subjects with IBS and IBD.

Statistical Analysis

A one-way ANOVA was conducted to compare symptom severity scores among the three gas patterns on LBT. Prevalence data was analyzed with a chi-square test.

B. Results:

Subjects

At the time of analysis, 772 patients were referred for a LBT and entered into the database. One hundred eighty-three subjects with negative breath tests, and 38 subjects either taking narcotic medications or with conditions predisposing to rapid transit, were excluded. A total of 551 subjects remained for analysis. Of these, 78 carried the diagnosis of TBD (49 with CD and 29 with UC) and 296 without TBD fulfilled Rome T criteria for IBS. Of the subjects with IBS, 120 reported constipation-predominant symptoms, 111 had diarrhea-predominant symptoms, and 65 had a constipation severity score equal to the diarrhea severity score.

Bacterial Overgrowth Analysis

Figure 7:
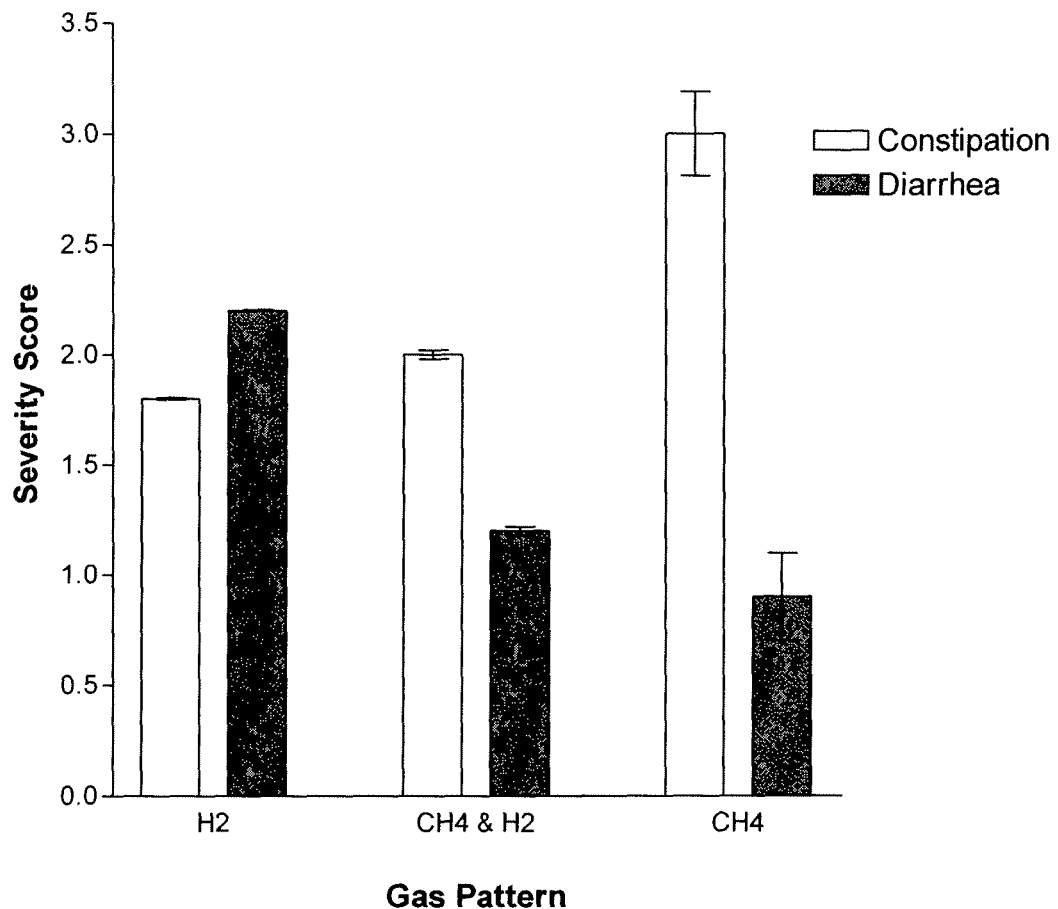
FIG. 7 shows mean diarrhea and constipation severity scores of all subjects (n=551) with SIBO as a function of the of type of gas pattern produced on LBT; p<0.00001 for trend in reduction of diarrhea with the presence of methane (one-way ANOVA); p<0.05 for the trend towards increasing constipation with the presence of methane (one-way ANOVA).

When the entire group of subjects with SIBO was evaluated (n=551), the diarrhea severity scores differed significantly among the three abnormal breath test patterns (one-way ANOVA, $p<0.00001$) (FIG. 7). Subjects who excreted methane reported significantly lower diarrhea severity scores than those who produced hydrogen only. Constipation severity also differed significantly among the breath test patterns ($p<0.05$), with higher severity scores reported by subjects who produced methane.

Figure 8:
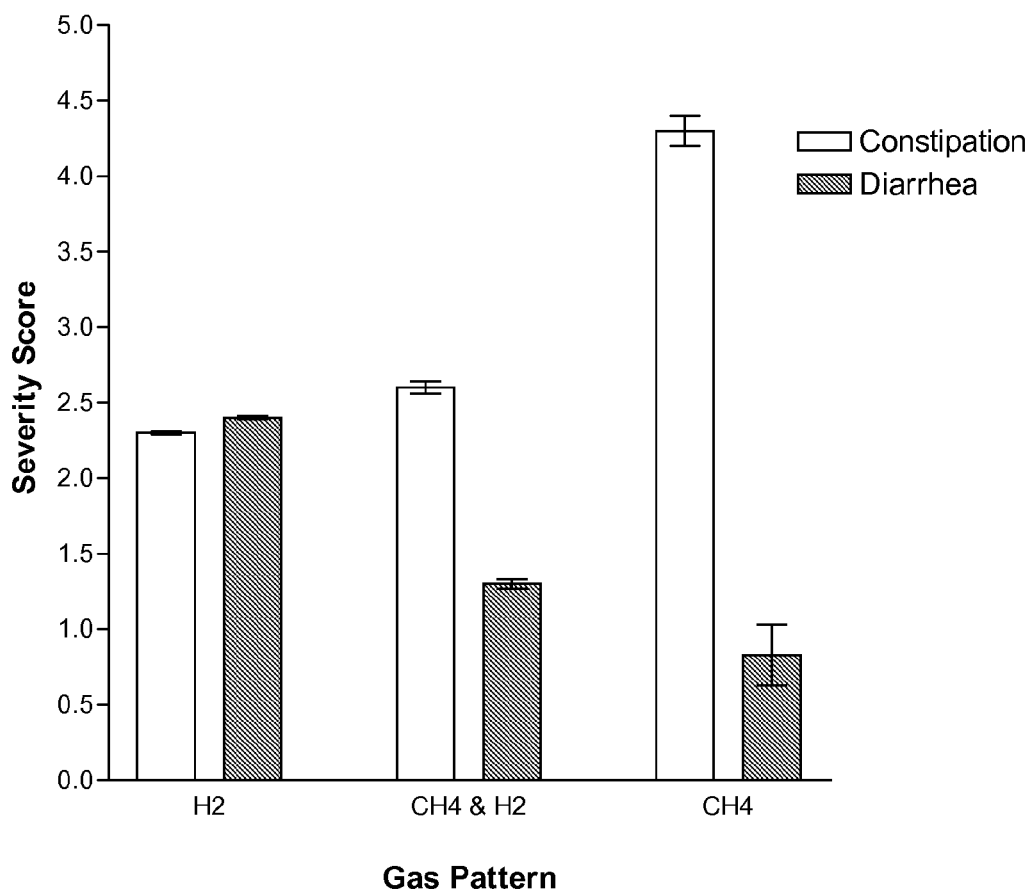
FIG. 8 shows mean diarrhea and constipation severity scores of IBS subjects (n=296) with SIBO as a function of the of type of gas pattern produced on LBT; p<0.001 for trend in reduction of diarrhea with the presence of methane (one-way ANOVA); p<0.05 for the trend towards increasing constipation with the presence of methane (one-way ANOVA).

Among all IBS subjects (n=296), diarrhea severity scores also differed similarly (one-way ANOVA, $p<0.001$) with lower severity reported by those who produced methane than those who produced hydrogen gas alone (FIG. 8).

Figure 9:
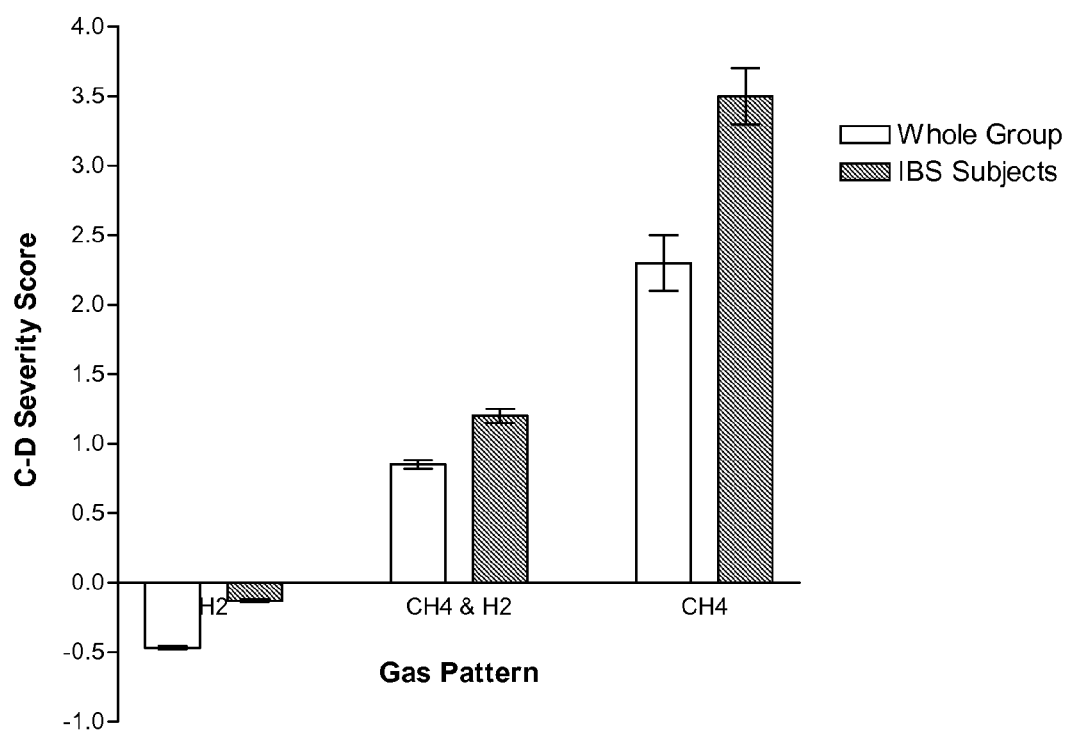
FIG. 9 shows mean constipation minus diarrhea (C-D) severity score for the whole group (n=551) and IBS subjects (n=296) as a function of the type of gas pattern produced on LBT; p<0.00001 for trend in C-D for whole group (one-way ANOVA); p<0.0001 for trend in C-D for IBS subjects (one-way ANOVA).

When the C-D score was evaluated as a reflection of the degree of constipation with respect to diarrhea, the effect of methane was even more obvious (FIG. 9). In both the total group and the IBS subjects, constipation was by far the prevailing symptom in individuals, whereas diarrhea was the prevailing symptom in subjects with only hydrogen.

Figure 10:
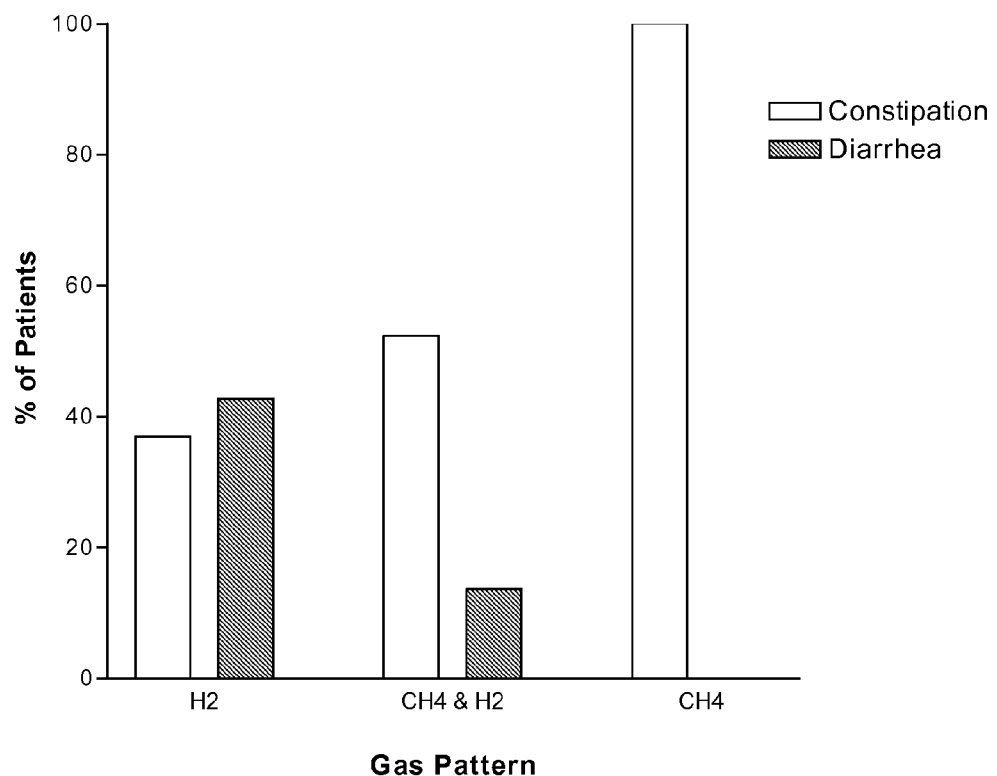
FIG. 10 shows the percentage of IBS subjects (n=296) exhibiting each gas pattern who reported constipation vs. diarrhea predominant symptoms.

When IBS subgroups were compared, constipation-predominant IBS was reported by 91 (37%) of the hydrogen-excreting subjects, 23 (52.3%) of the hydrogen and methane-excreting subjects and 6 (100%) of the methane-excreting subjects. By contrast, diarrhea-predominant IBS was observed in 105 (42.7%) of the hydrogen excretors, 6 (13.6%) of the hydrogen and methane excretors, and none of the methane excretors (FIG. 10).

Inflammatory Bowel Disease and Methane

Figure 11:
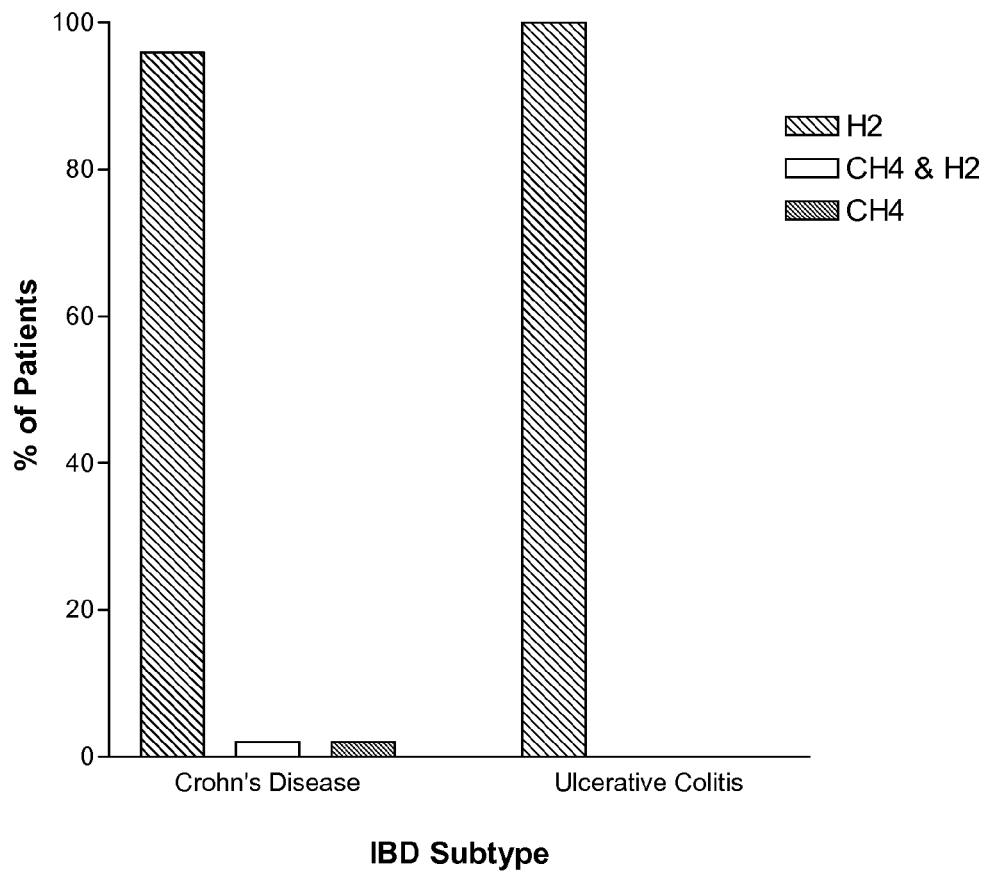
FIG. 11 shows the percentage of subjects with IBD who produced each of the three abnormal gas patterns on LBT.

The predominant gas excreted by patients with IBD was hydrogen alone, detected in 47 of 49 subjects (95.9%) with Crohn's disease and 29 of 29 (100%) subjects (100%) with ulcerative colitis. (FIG. 11).

Methane Production Between Subjects with IBS and IBD

The percentage of subjects with IBS who produced each of the three gas patterns was tabulated. Of 296 IBS subjects, 246 (83.1%) produced hydrogen gas alone, 44 (14.9%) produced hydrogen and methane gas, and 6 (2.0%) produced methane gas alone. Methane production depended significantly upon whether or not subjects had IBS or IBD. IBS subjects were more likely to produce methane gases than subjects with ulcerative colitis or Crohn's disease (OR 7.7, CI 1.8-47.0, $p<0.01$) (Table 4).

TABLE 4

Comparison of prevalence of methane to non-methane gas production between subjects with IBS and IBD.

| Disease Type | CH4 | Non-CH4 |
| --- | --- | --- |
| IBS (n = 296) | 50 | 246 |
| UC or CD (n = 82) | 2 | 76 |

Chi square 9.4, OR 7.7, CI 1.8-47.0, p-value < 0.01

REFERENCES CITED

1. Drossman D A, Sandler R S, McKee D L, Lovitz A J. Bowel patterns among subjects not seeking health care. Gastroenterology 1982; 83:529-34.
2. Thompson W G, Heaton K W. Functional bowel disorders in apparently healthy people. Gastroenterology 1980; 79:283-8.
3. Kumar D, Wingate D L. The irritable bowel syndrome: a paroxysmal motor disorder. Lancet 1985; 2:973-77.
4. Grundy D. Mechanisms for the symptoms of irritable bowel disease-possible role of vagal afferents. In, Neurogastroenterology from the Basics to the Clinics. H-J Krammer and M V Singer, Editors, Klumer Academic Publishers, Boston, 2000, pp. 659-663.
5. Silverman D H S, Munakata J A, Ennes H, Mandelkern M A, Hoh C K, Mayer E A. Regional cerebral activity in normal and pathological perception of visceral pain. Gastroenterology 1997; 112:64-72.
6. Whitehead W E, Crowell M D, Robinson J C, Heller B R, Schuster M M. Effects of stressful life events on bowel symptoms: Subjects with irritable bowel syndrome compared with subjects without bowel dysfunction. Gut 1992; 33:825-30.
7. Drossman D A, Richter J E, et al., eds. Functional gastrointestinal disorders: diagnosis, pathophysiology and treatment: a multinational consensus. Boston: Little, Brown, 1994.
8. Thompson W G, Longstreth G F, Drossman D A, Heaton K W, Irvine E J, Müller-Lissner S A. Functional bowel disorders and functional abdominal pain. Rome II: A multinational consensus document on functional gastrointestinal disorders. Gut 1999; 45:1143-47.
9. Kruis W, Thieme C H, Weinzierl M, Schüssler P, Holl J, Paulus W. A diagnostic score for the irritable bowel syndrome. Gastroenterology 1984; 87:1-7.
10. Sullivan S N. A prospective study of unexplained visible abdominal bloating. N Z Med J 1994; 107:428-30.
11. Koide A, Yamaguchi T, Odaka T, et al. Quantitative analysis of bowel gas using plain abdominal radiograph in patients with irritable bowel syndrome. Am J Gastroenterol 2000; 95:1735-41.
12. Pimentel M, Chow E J, Lin H C. Eradication of small intestinal bacterial overgrowth reduces symptoms of irritable bowel syndrome. Am J Gastro 2000; 95:3503-6.
13. Fiedorek S C, Pumphrey C L, Casteel H B. Breath methane production in children with constipation and encorparesis. J Pediatr Gastroenterol 1990; 10:473-77.
14. Fass R, Longstreth G F, Pimentel M, Fullerton S, Russak S M, Chiou C-F, Reyes E, Crane P, Eisen G, McCarberg B, Ofman J. Evidence and consensus-based practice guidelines for the diagnosis of irritable bowel syndrome. Arch Intern Med 2001; 161:2081-8.
15. Veldhuyzen Van Zanten S J O, Talley N J, Bytzer P, Klein K B, Whorwell P J, Zinsmeister A R. Design of treatment trials for functional gastrointestinal disorders. Gut 1999; 45:1169-77.

16. Whitehead W E, Corazziari E, Prizont R, Senior J R, Thompson W G, Veldhuyzen Van Zanten S J O. Definition of a responder in clinical trials for functional gastrointestinal disorders: report on a symposium. Gut 1999; 45(Suppl II):II78-9.
17. Camilleri M, Northcutt A R, Kong S, Dukes G E, McSorley D, Mangel A W. Efficacy and safety of alosetron in women with irritable bowel syndrome: a randomized, placebo-controlled trial. Lancet 2000; 355:1035-40.
18. Bond J H Jr., Levitt M D. Investigation of small bowel transit time in man utilizing pulmonary hydrogen (H2) measurements. J Lab Clin Med 1975; 85:546-555.
19. Joseph F Jr, Rosenberg A J. Breath testing: diseased versus normal patients. J Pediatr Gastroenterol 1988; 7:787-8.
20. Galatola G, Grosso M, Barlotta A, et al. Diagnosis of bacterial contamination of the small intestine using the 1 g [14C] xylose breath test in various gastrointestinal diseases. Menerva Gastroenterologic Dietologica 1991; 37:169-75.
21. Nayak A, Karnad D, Abraham P, Mistry F P. Metronidazole relieves symptoms in irritable bowel syndrome: the confusion with so-called 'chronic amebiasis'. Indian J Gastroenterol 1997; 16:137-9.
22. King T S, Elia M, Hunter J O. Abnormal colonic fermentation in irritable bowel syndrome. Lancet 1998; 352:1187-9.
23. Neal K R, Hebden J, Spiller R. Prevalence of gastrointestinal symptoms six months after bacterial gastroenteritis and risk factors for development of the irritable bowel syndrome: postal survey of patients. BMJ 1997; 314:779-82.
24. Collins S M, Barbara G, Vallance B. Stress, inflammation and the irritable bowel syndrome. Canadian Journal of Gastroenterology 1999; 13:47A-49A.
25. Weaver G A, Krause J A, Miller T L, Wollin M J. Incidence of methanogenic bacteria in a sigmoidoscopy population: an association of methanogenic bacteria and diverticulosis. Gut 1986; 27:698-704.
26. Bjorneklett A, Fausa O, Midtvedt T. Bacterial overgrowth in jejunal and ileal disease. Scand J Gastroenterol 1983; 18:289-98.
27. McKay L F, Eastwood M A, Brydon W G. Methane excretion in man-a study of breath, flatus and faeces. Gut 1985; 26:69-74.
28. Castiglione F, Blanco G D V, Rispo A, et al. Orocecal transit time and bacterial overgrowth in patients with Crohn's disease. J Clin Gastroenterol 2000; 31:63-66.
29. Riordan S M, McIvor C J, Walker B M, Duncombe V M, Bolin T D, Thomas M C. The lactulose hydrogen breath test and small intestinal bacterial overgrowth. Am J Gastroenterol 1996; 91:1795-1803.
30. Bentley D W, Nichols R L, Condon R E, Gorbach S L. The microflora of the human ileum and intrabdominal colon: results of direct needle aspiration at surgery and evaluation of the technique. J Lab Clin Med 1972; 79:421-9.
31. Gorbach S L. Intestinal Microflora. Gastroenterology 1971; 60:1110-29.
32. Nichols R L, Condon R E, Bentley D W, Gorbach S L. Ileal microflora in surgical patients. J Urol 1971; 105:351-3.
33. Plaut A G, Gorbach S L, Nahas L, Weinstein L, Spanknebel G, Levitan R. Studies of intestinal microflora. 3. The microbial flora of human small intestinal mucosa and fluids. Gastroenterology 1967; 53:868-73.
34. Cann P A, Read N W, Brown C, Hobson N, Holdsworth C D. Irritable bowel syndrome: relationship of disorders in the transit of a single solid meal to symptom patterns. Gut 1983; 24:405-11.
35. Read N W, Al-Janabi M N, Hogate A M, Barber D S, Edwards C A. Simultaneous measurement of gastric emptying, small bowel residence and colonic filling of a solid meal by the use of the gamma camera. Gut 1986; 27:300-8.
36. Hutchinson R, Notghi A, Smith N B, Harding L K, Kumar D. Scintigraphic measurement of ileocaecal transit in irritable bowel syndrome and chronic idiopathic constipation. Gut 1995; 36:585-9.
37. Rhodes J M, Middleton P, Jewell D P. The lactulose hydrogen breath test as a diagnostic test for small intestinal bacterial overgrowth. Scand J Gastroenterol 1979; 14:333-6.
38. Kerlin P, Wong L. Breath hydrogen testing in bacterial overgrowth of the small intestine. Gastroentero l 1988; 95:982-8.
39. Rutgeerts P, Ghoos Y, Vantrappen G, Eyssen H. Ileal dysfunction and bacterial overgrowth in patients with Crohn's disease. European J Clin Invest 1981; 11:199-206.
40. Funayama Y, Sasaki I, Naito H, et al. Monitoring and antibacterial treatment for postoperative bacterial overgrowth in Crohn's disease. Diseases of the Colon and Rectum 1999; 42:1072-7.
41. Peled Y, Weinberg D, Hallak A, et al. Factors affective methane production in humans. Gastrointestinal diseases and alterations of colonic flora. Dig Dis Sci 1987; 32:267-71.
42. Melcher E A, Levitt M D, Slavin J L. Methane production and bowel function parameters in healthy subjects on low- and high fiber diets. Nutrition and Cancer 1991; 16:85-92.
43. Levitt M D, Ingelfinger F J. Hydrogen and methane production in man. Annals of the New York Academy of Sciences. 1968; 150:75-81.

The invention claimed is:

1. A method of treating constipation-predominant irritable bowel syndrome (C-IBS), comprising administering an effective amount of a selective inhibitor of methanogenesis to the distal gut of a human patient in need thereof, wherein:
   the C-IBS is characterized by elevated intestinal methane levels and
   the selective inhibitor of methanogenesis is a HMG-CoA reductase inhibitor.
2. The method of claim 1, wherein the method inhibits the growth of methanogenic bacteria in the human patient.
3. The method of claim 1, wherein the method reduces the partial pressure of methane in the human patient's intestines.
4. The method of claim 1, wherein the method reduces the partial pressure of methane in the human patient's intestines as assessed by methane breath testing.
5. The method of claim 1, wherein the HMG-CoA reductase inhibitor is administered enterally.
6. The method of claim 5, wherein the HMG-CoA reductase inhibitor is administered orally.

* * * * *